United States Patent
Ye et al.

(10) Patent No.: US 9,982,275 B2
(45) Date of Patent: May 29, 2018

(54) PROMOTERS, EXPRESSION CASSETTES, VECTORS, KITS, AND METHODS FOR THE TREATMENT OF ACHROMATOPSIA AND OTHER DISEASES

(71) Applicant: Applied Genetic Technologies Corporation, Alachua, FL (US)

(72) Inventors: Guo-Jie Ye, Gainesville, FL (US); Jeffrey D. Chulay, Southern Pines, NC (US)

(73) Assignee: Applied Genetic Technologies Corporation, Alachua, FL (US)

(*) Notice: Subject to any disclaimer, the term of this patent is extended or adjusted under 35 U.S.C. 154(b) by 724 days.

(21) Appl. No.: 13/936,728

(22) Filed: Jul. 8, 2013

(65) Prior Publication Data

US 2013/0317091 A1   Nov. 28, 2013

Related U.S. Application Data

(63) Continuation of application No. PCT/US2012/020423, filed on Jan. 6, 2012.

(60) Provisional application No. 61/430,710, filed on Jan. 7, 2011.

(51) Int. Cl.
| | | |
|---|---|---|
| *C12N 15/85* | (2006.01) | |
| *C07K 14/705* | (2006.01) | |
| *A61K 48/00* | (2006.01) | |

(52) U.S. Cl.
CPC .......... *C12N 15/85* (2013.01); *C07K 14/705* (2013.01); *A61K 48/0058* (2013.01); *C12N 2799/025* (2013.01); *C12N 2830/008* (2013.01)

(58) Field of Classification Search
CPC ... C07K 14/705; A61K 48/0058; C12N 15/85
See application file for complete search history.

(56) References Cited

U.S. PATENT DOCUMENTS

| 6,225,112 B1 | 5/2001 | Sakai et al. |
|---|---|---|
| 2003/0003582 A1 | 1/2003 | Wakefield et al. |
| 2010/0081707 A1 | 4/2010 | Ali et al. |

FOREIGN PATENT DOCUMENTS

| EP | 1302539 A1 | 4/2003 |
|---|---|---|
| EP | 1600511 A1 | 11/2005 |
| JP | 06-165679 | 6/1994 |
| JP | 2003-146909 | 5/2003 |
| WO | WO-2005/039643 A2 | 5/2005 |
| WO | WO-2007078599 A2 | 7/2007 |
| WO | WO-2008073303 A2 | 6/2008 |
| WO | 2009097129 A1 | 8/2009 |

OTHER PUBLICATIONS

Alexander et al (Nat Med, 13(6): 685-687, 2007).*
Komaromy et al (Human Molecular Genetics, 19(23): 2581-2593, 2010).*
Komaromy, A. M. et al. "Gene therapy rescues cone function in congenital achromatopsia" Human Molecular Genetics, vol. 19 (13), pp. 2581-2593 (Apr. 8, 2010).
Carvalho, L.S. et al. "Long-term and age-dependent restoration of visual function in a mouse model of CNGB3-associated achromatopsia following gene therapy." Human Molecular Genetics, vol. 20, No. 16, May 15, 2011, pp. 3161-3175.
Coburn, C.M. et al. "A Putative Cyclic Nucleotide-Gated Channel Is Required for Sensory Development and Function in C. elegens." Neuron, vol. 17, No. 4, Oct. 1, 1996, pp. 695-706.
GenBank Submission: NIH/NCBI, Accession No. NG_016980; GI: 293597526, Kohl et al., Apr. 3, 2010.
Roni, V. "*Homo sapiens* cyclic nucleotide gated channel beta 3 (CNGB3) mRNA, part." Database EMBL, Accession No. DQ426865, Feb. 20, 2007, 1 page.
Roni, V. et al. "Mapping of transcripotion start sites of human retina expressed genes." BMC Genomics, vol. 8, No. 42, Feb. 7, 2007, 14 pages.
Danko, C. G. et al. "Bioinformatic identification of novel putative photoreceptor specific cis-elements," BMC Bioinformatics, Biomed Central, vol. 8(2), Oct. 22, 2007, pp. 1-16.

* cited by examiner

*Primary Examiner* — Anoop K Singh
*Assistant Examiner* — Magdalene K Sgagias
(74) *Attorney, Agent, or Firm* — McCarter & English, LLP; Jonathan M. Sparks

(57) ABSTRACT

The present invention provides isolated promoters, transgene expression cassettes, vectors, kits, and methods for treatment of genetic diseases that affect the cone cells of the retina.

10 Claims, 8 Drawing Sheets

Figure 5

SEQ ID NO: 1:

agccgccatcaggaataaacaaaacattcattttgggaaaaaccccaaactgtcagacacagcatccaaacaaaacagaccatttttctcctg
cagttggcatattttggttttgcatttacaagtaattttgagcattgtctgcaaaaacatttctcacaaaaagaaggcagtttggtttggggacatc
ttcgttccacattctcttacagagcttacatagcacctctctctccattctccagccagcctgctaaattccaggcttatttacaataagcaatctag
acagaccagaaatgtcctgctaaaaaagtttcataaatagggactccctggtatctttccactgataaatactatgagatttatacgaaagtctg
gtgaggtcattttttcctctgcaggtcttaggaagggaaaaaattagtcacaggctggctgttaacaccttcccttcctttggcttagcttctatgc
ttatacccaaagttcaaaatgtaatcaattacaggattacaggattatctgaaaagttcctaaaatggccctatacatatttgataatctattcaga
attatttctgaagcaataatggaaccaaaacacccccaccatttttaacaaaaataaatagctttgtgtttccaggccatataagtcaaatcat
gtattcaattacgttatttattaggtaagtttattttgataaaatggttgaatctaaaattaaaacttctaatttattttaaaaatccataagggaactg
cgattttggtaatatgaaatctaaattaaaatgctttcttcataaatacttaaaggcttttttctgtattaactgtaataaacgtatcttaaaatacataa
ctagtatctcaaggaaatttccagattgcaaaaatacagagggcaagaagtatttgatgggttgacttaggctgccctgggtgtgggtgtgtac
cttgttgcataaaggctttggttttaatttgaaactgcagaagataagtgctctcattaaaaacaaaaacaaaaacagaaccccttttaaaaaaaa
tcatgcgtctttggtgcactaaaaaatctcatccaacagcatagaacatcaactttgtctgggctccgggcaaaggggaaaaaaagttctctt
taacaaatcttagtcttgtatctttgcctcacacaggtttggggtcaaaagtgacacacacacacacagaggcagagtagaataagcagatttt
tttttgtttagccatgtggaaatcaaccaccagaagaacagaaaaagaaagcttaaaaatagtggcctaacattgcaggaccagagaaggg
gattttgaggagtgaatgagttgcttcatatcataagccctcatggattttttttaatcatttccatattactttgcataaagttagacagataaagat
aagtaggtgggtaattagaaggaaaaaaaagaaagaaaacaatgtgttgtgtgatcacatttaaaccattcaaatcaactatgaagctgtgtt
taatcctctacttctaaattattcacaagatcattttgactccctaaagttcataaacagagtgcaaatcacccaagcagaagtattttgctgcttt
aagccaaagccctgactagctaaggagttgcctgtaggaattaaccagaacaaaatcctgattaaacagctaattggcttgtctactaaagaa
aaggaaaacaaagtacatttctctaccttaaggcacagtcataaatacagagggttttcagaaccacc

Figure 5 Con't

SEQ ID NO: 2 gtaccacattctcttacagagcttacatagcacctctctctccattctccagccagcctgctaaattccaggcttatttacaataagcaatctaga
cagaccagaaatgtcctgctaaaaaagtttcataaatagggactccctggtatctttccactgataaatactatgagatttatacgaaagtctggt
gaggtcattttttcctctgcaggtcttaggaagggaaaaaattagtcacaggctggctgttaacaccttcccttccttggcttagcttctatgctt
atacccaaagttcaaaatgtaatcaattacaggattacaggattatctgaaaagttcctaaaatggccctatacatatttgataatctattcagaat
tatttctgaagcaataatggaaccaaaacacccccaccattttttaacaaaaataaatagctttgtgtttccaggccatataagtcaaatcatgt
attcaattacgttatttattaggtaagtttattttgataaaatggttgaatctaaaattaaaacttctaatttatttaaaaatccataagggaactgcg
attttggtaatatgaaatctaaattaaaatgctttcttcataaatacttaaaggcttttttctgtattaactgtaataaacgtatcttaaaatacataacta
gtatctcaaggaaatttccagattgcaaaaatacagagggcaagaagtatttgatgggttgacttaggctgccctgggtgtgggtgtgtacctt
gttgcataaaggctttggttttaatttgaaactgcagaagataagtgctctcattaaaaacaaaaacaaaaacagaaccccttttaaaaaaaatca
tgcgtctttggtgcactaaaaaatctcatccaacagcatagaacatcaactttgtctgggctccgggcaaggggaaaaaaaagttctctttaa
caaatcttagtcttgtatctttgcctcacacaggtttggggtcaaaagtgacacacacacacacagaggcagagtagaataagcagatttttttt
tgtttagccatgtggaaatcaaccaccagaagaacagaaaaagaaagcttaaaaatagtggcctaacattgcaggaccagagaagggatt
ttgaggagtgaatgagttgcttcatatcataagccctcatggatttttttaatcatttccatattactttgcataaagttagacagatataagataagt
aggtgggtaattagaaggaaaaaaaagaaagaaaacaatgtgttgtgtgatcacatttaaaccattcaaatcaactatgaagctgtgtttaat
cctctacttctaaattattcacaagatcatttgactccctaaagttcataaacagagtgcaaatcacccaagcagaagtatttgctgcttttaag
ccaaagccctgactagctaaggagttgcctgtaggaattaaccagaacaaaatcctgattaaacagctaattggcttgtctactaaagaaaag
gaaaacaaagtacatttctctaccttaaggcacagtcataaatacagagggttttcagaaccacc

SEQ ID NO: 3 ctcagatctgaattcggtacctagttattaatagtaatcaattacggggtcattagttcatagcccatatatggagttccgcgttacataacttacg
gtaaatggcccgcctggctgaccgcccaacgacccccgcccattgacgtcaataatgacgtatgttcccatagtaacgccaatagggacttt
ccattgacgtcaatgggtggagtatttacggtaaactgcccacttggcagtacatcaagtgtatcatatgccaagtacgccccctattgacgtc
aatgacggtaaatggcccgcctggcattatgcccagtacatgaccttatgggactttcctacttggcagtacatctac

Figure 5 con't

SEQ ID NO:4 aacaccttcccttcctttggcttagcttctatgcttatacccaaagttcaaaatgtaatcaattacaggattacaggattatctgaaaagttcctaaa
atggccctatacatatttgataatctattcagaattatttctgaagcaataatggaaccaaaacaccccccaccattttttaacaaaaataaatagc
tttgtgtttccaggccatataagtcaaatcatgtattcaattacgttatttattaggtaagtttattttgataaaatggttgaatctaaaattaaaacttc
taatttattttaaaaatccataagggaactgcgatttggtaatatgaaatctaaattaaaatgctttcttcataaatacttaaaggcttttttctgtatta
actgtaataaacgtatcttaaaatacataactagtatctcaaggaaatttccagattgcaaaaatacagagggcaagaagtatttgatgggttga
cttaggctgccctgggtgtgggtgtgtaccttgttgcataaaggctttggtttaatttgaaactgcagaagataagtgctctcattaaaaacaaa
aacaaaaacagaacccctttaaaaaaaatcatgcgtctttggtgcactaaaaaatctcatccaacagcatagaacatcaactttgtctgggctc
cgggcaaaggggaaaaaaaagttctctttaacaaatcttagtcttgtatctttgcctcacacaggtttggggtcaaaagtgacacacacacaca
cagaggcagagtagaataagcagatttttttttgtttagccatgtggaaatcaaccaccagaagaacagaaaaagaaagcttaaaaatagtgg
cctaacattgcaggaccagagaaggggattttgaggagtgaatgagttgcttcatatcataagccctcatggattttttttaatcatttccatatta
ctttgcataaagttagacagataaagataagtaggtgggtaattagaaggaaaaaaaaagaaagaaaacaatgtgttgtgtgatcacatttaa
accattcaaatcaactatgaagctgtgtttaatcctctacttctaaattattcacaagatcattttgactccctaaagttcataaacagagtgcaaat
cacccaagcagaagtattttgctgcttttaagccaaagccctgactagctaaggagttgcctgtaggaattaaccagaacaaaatcctgattaa
acagctaattggcttgtctactaaagaaaaggaaaacaaagtacatttctctaccttaaggcacagtcataaatacagagggttttcagaacca
cc

SEQUENCE LISTING

```
<160> NUMBER OF SEQ ID NOS: 14

<210> SEQ ID NO 1
<211> LENGTH: 1796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
agccgccatc aggaataaac aaaacattca tttgggaaa accccaaac tgtcagacac      60 agcatccaaa caaaacagac cattttctc ctgcagttgg catattttgg ttttgcattt    120
acaagtaatt tttgagcatt gtctgcaaaa acatttctca caaaagaag gcagtttggt    180 ttggggacat cttcgttcca cattctctta cagagcttac atagcacctc tctctccatt    240
ctccagccag cctgctaaat tccaggctta tttacaataa gcaatctaga cagaccagaa    300
atgtcctgct aaaaagttt cataaatagg gactccctgg tatctttcca ctgataaata    360
ctatgagatt tatacgaaag tctggtgagg tcatttttc ctctgcaggt cttaggaagg    420
gaaaaaatta gtcacaggct ggctgttaac accttccctt cctttggctt agcttctatg    480 cttatacccca agttcaaaa tgtaatcaat tacaggatta caggattatc tgaaaagttc    540
ctaaaatggc cctatacata tttgataatc tattcagaat tatttctgaa gcaataatgg    600
aaccaaaaca cccccaccaa tttttaaca aaaataaata gctttgtgtt tccaggccat    660
ataagtcaaa tcatgtattc aattacgtta tttattaggt aagtttattt ttgataaaat    720
ggttgaatct aaaattaaa cttctaattt atttaaaaa tccataaggg aactgcgatt     780
ttggtaatat gaaatctaaa ttaaatgct ttcttcataa atacttaaag gctttttct      840 gtattaactg taataaacgt atcttaaaat acataactag tatctcaagg aaatttccag    900
attgcaaaaa tacagagggc aagaagtatt tgatggttg acttaggctg ccctgggtgt    960
gggtgtgtac cttgttgcat aaaggctttg gtttaattt gaaactgcag aagataagtg   1020
ctctcattaa aaacaaaaac aaaaacagaa cccctttaaa aaaaatcatg cgtctttggt   1080
gcactaaaaa atctcatcca acagcataga acatcaactt tgtctgggct ccgggcaaag   1140
```

```
gggaaaaaaa agttctctttt aacaaatctt agtcttgtat ctttgcctca cacaggtttg    1200
gggtcaaaag tgacacacac acacacagag gcagagtaga ataagcagat ttttttttgt    1260
ttagccatgt ggaaatcaac caccagaaga acagaaaaag aaagcttaaa aatagtggcc    1320
taacattgca ggaccagaga aggggatttt gaggagtgaa tgagttgctt catatcataa    1380
gccctcatgg attttttta atcatttcca tattactttg cataaagtta gacagataaa    1440
gataagtagg tgggtaatta aaggaaaaa aaagaaaga aaacaatgtg ttgtgtgatc    1500
acatttaaac cattcaaatc aactatgaag ctgtgtttaa tcctctactt ctaaattatt    1560
cacaagatca ttttgactcc ctaaagttca taaacagagt gcaaatcacc caagcagaag    1620
tattttgctg cttttaagcc aaagccctga ctagctaagg agttgcctgt aggaattaac    1680
cagaacaaaa tcctgattaa acagctaatt ggcttgtcta ctaaagaaaa ggaaaacaaa    1740
gtacatttct ctaccttaag gcacagtcat aaatacagag ggttttcaga accacc       1796
```

<210> SEQ ID NO 2
<211> LENGTH: 1602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gtaccacatt ctcttacaga gcttacatag cacctctctc tccattctcc agccagcctg      60
ctaaattcca ggcttattta caataagcaa tctagacaga ccagaaatgt cctgctaaaa     120
aagtttcata aatagggact ccctggtatc tttccactga taaatactat gagatttata     180
cgaaagtctg gtgaggtcat ttttttcctct gcaggtctta ggaagggaaa aaattagtca     240
caggctggct gttaacacct tcccttcctt tggcttagct tctatgctta tacccaaagt     300
tcaaaatgta atcaattaca ggattacagg attatctgaa aagttcctaa aatgccccta     360
tacatatttg ataatctatt cagaattatt tctgaagcaa taatggaacc aaaacacccc     420
ccaccatttt ttaacaaaaa taatagctt tgtgtttcca ggccatataa gtcaaatcat     480
gtattcaatt acgttattta ttaggtaagt ttattttga taaaatggtt gaatctaaaa     540 ttaaacttc taatttattt taaaaatcca taagggaact gcgatttggg taatatgaaa     600
tctaaattaa aatgctttct tcataaatac ttaaaggctt ttttctgtat taactgtaat     660
aaacgtatct taaatacat aactagtatc tcaaggaaat ttccagattg caaaaatcaca     720 gagggcaaga agtatttgat gggttgactt aggctgccct gggtgtgggt gtgtaccttg     780
ttgcataaag gctttggttt taatttgaaa ctgcagaaga taagtgctct cattaaaaac     840
aaaaacaaaa acagaacccc tttaaaaaaa atcatgcgtc tttggtgcac taaaaaatct     900
catccaacag catagaacat caactttgtc tgggctccgg gcaagggga aaaaaaagtt     960 ctctttaaca aatcttagtc ttgtatcttt gcctcacaca ggtttgggt caaaagtgac    1020 acacacacac acagaggcag agtagaataa gcagatttttt ttttgtttag ccatgtggaa    1080
atcaaccacc agaagaacag aaaaagaaag cttaaaaata gtggcctaac attgcaggac    1140
cagagaaggg gattttgagg agtgaatgag ttgcttcata tcataagccc tcatggattt    1200
tttttaatca tttccatatt actttgcata aagttagaca gataaagata agtaggtggg    1260
taattagaag gaaaaaaaa gaaagaaaac aatgtgttgt gtgatcacat ttaaaccatt    1320
caaatcaact atgaagctgt gtttaatcct ctacttctaa attattcaca agatcatttt    1380
```

```
gactccctaa agttcataaa cagagtgcaa atcacccaag cagaagtatt ttgctgcttt    1440
taagccaaag ccctgactag ctaaggagtt gcctgtagga attaaccaga acaaaatcct    1500
gattaaacag ctaattggct tgtctactaa agaaaggaa acaaagtac atttctctac     1560 cttaaggcac agtcataaat acagagggtt ttcagaacca cc                      1602
```

<210> SEQ ID NO 3
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ctcagatctg aattcggtac ctagttatta atagtaatca attacggggt cattagttca     60
tagcccatat atggagttcc gcgttacata acttacggta aatggcccgc ctggctgacc    120
gcccaacgac ccccgcccat tgacgtcaat aatgacgtat gttcccatag taacgccaat    180
agggactttc cattgacgtc aatgggtgga gtatttacgg taaactgccc acttggcagt    240
acatcaagtg tatcatatgc caagtacgcc ccctattgac gtcaatgacg gtaaatggcc    300
cgcctggcat tatgcccagt acatgacctt atgggacttt cctacttggc agtacatcta    360
c                                                                    361
```

<210> SEQ ID NO 4
<211> LENGTH: 1349
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
aacaccttcc cttcctttgg cttagcttct atgcttatac ccaaagttca aaatgtaatc     60
aattacagga ttacaggatt atctgaaaag ttcctaaaat ggccctatac atatttgata    120
atctattcag aattatttct gaagcaataa tggaaccaaa acaccccca ccatttttta    180 acaaaaataa atagctttgt gtttccaggc catataagtc aaatcatgta ttcaattacg    240
ttatttatta ggtaagttta ttttgataa atggttgaa tctaaaatta aaacttctaa     300
tttattttaa aaatccataa gggaactgcg attttggtaa tatgaaatct aaattaaaat    360
gctttcttca taaatactta aaggcttttt tctgtattaa ctgtaataaa cgtatcttaa    420
aatacataac tagtatctca aggaaatttc cagattgcaa aaatacagag ggcaagaagt    480
atttgatggg ttgacttagg ctgccctggg tgtgggtgtg taccttgttg cataaaggct    540
ttggttttaa tttgaaactg cagaagataa gtgctctcat taaaaacaaa acaaaaaca    600 gaaccccttt aaaaaaaatc atgcgtcttt ggtgcactaa aaaatctcat ccaacagcat    660
agaacatcaa ctttgtctgg gctccgggca aaggggaaaa aaaagttctc tttaacaaat    720
cttagtcttg tatctttgcc tcacacaggt ttggggtcaa aagtgacaca cacacacaca    780
gaggcagagt agaataagca gatttttttt tgtttagcca tgtggaaatc aaccaccaga    840
agaacagaaa aagaaagctt aaaaatagtg gcctaacatt gcaggaccag agaagggat    900 tttgaggagt gaatgagttg cttcatatca taagccctca tggattttt ttaatcattt    960 ccatattact ttgcataaag ttagacagat aaagataagt aggtgggtaa ttagaaggaa   1020
```

-continued

```
aaaaaaagaa agaaaacaat gtgttgtgtg atcacattta aaccattcaa atcaactatg    1080
aagctgtgtt taatcctcta cttctaaatt attcacaaga tcattttgac tccctaaagt    1140
tcataaacag agtgcaaatc acccaagcag aagtattttg ctgcttttaa gccaaagccc    1200
tgactagcta aggagttgcc tgtaggaatt aaccagaaca aaatcctgat taaacagcta    1260
attggcttgt ctactaaaga aaaggaaaac aaagtacatt tctctacctt aaggcacagt    1320
cataaataca gagggttttc agaaccacc                                     1349
```

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
gatttaagct tgcggccgcg ggtacaattc cgcagctttt agag                      44
```

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ctgcaagctt gtgggaccac aaatcag                                         27
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tagcggtacc agccatcggc tgttag                                          26
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gtgggtaccg gaggctgagg ggtg                                            24
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
cagactagcc agaatcacag atc                                             23
```

<210> SEQ ID NO 10

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctcctatag gcttcacctt gttg                                          24

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttgggtacc agccgccatc aggaataaac                                    30

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctccgcggt ggttctgaaa accctc                                        26

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
catcttggta ccacattctc ttacagagc                                     29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atcttctcga gggtggttct gaaaaccctc                                    30
```

PROMOTERS, EXPRESSION CASSETTES, VECTORS, KITS, AND METHODS FOR THE TREATMENT OF ACHROMATOPSIA AND OTHER DISEASES

RELATED APPLICATIONS

This application is a continuation of International Application No. PCT/US2012/20423, filed Jan. 6, 2012, which claims the benefit of U.S. Provisional Application No. 61/430,710, filed on Jan. 7, 2011. The entire contents of each of the aforementioned application is hereby expressly incorporated herein by reference.

SEQUENCE LISTING

The instant application contains a Sequence Listing which has been submitted electronically in ASCII format and is hereby incorporated by reference in its entirety. Said ASCII copy, created on Jul. 27, 2016, is named 119561-00702_SL.txt and is 10, 081 bytes in size.

BACKGROUND OF THE INVENTION

Achromatopsia is a color vision disorder, which is typically a congenital autosomal recessive disorder. It may be partial or complete. See Pang, J.-J. et al. (2010). Achromatopsia as a Potential Candidate for Gene Therapy. In *Advances in Experimental Medicine and Biology*, Volume 664, Part 6, 639-646 (2010) (hereinafter Pang et al). Symptoms of achromatopsia include reduced visual acuity, achromatopia (lack of color perception), hemeralopia (reduced visual capacity in bright light accompanied by photoaversion, meaning a dislike or avoidance of bright light), nystagmus (uncontrolled oscillatory movement of the eyes), iris operating abnormalities, and impaired stereovision (inability to perceive three-dimensional aspects of a scene).

Electroretinograms reveal that in achromatopsia, the function of retinal rod photoreceptors remains intact, whereas retinal cone photoreceptors are not functional. The rod and cone photoreceptors serve functionally different roles in vision. Pang et al. Cone photoreceptors are primarily responsible for central, fine resolution and color vision while operating in low to very bright light. They are concentrated in the central macula of the retina and comprise nearly 100% of the fovea. Rod photoreceptors are responsible for peripheral, low light, and night vision; they are found primarily outside the macula in the peripheral retina.

Approximately 1 in 30,000 individuals suffers from complete achromatopsia. In complete achromatopsia, there is total color vision loss, central vision loss, and visual acuity of 20/200 or worse. Thus, most individuals with achromatopsia are legally blind. The current standard of care consists of limiting retinal light exposure with tinted contact lenses and providing magnification to boost central vision. However, there is no treatment available that corrects cone function in achromatopsia. Pang et al.

There are various genetic causes of congenital achromatopsia. Mutations in the cyclic nucleotide-gated ion channel beta 3 (CNGB3, also known as ACHM3) gene, are one genetic cause of achromatopsia. Recent studies in dogs suggest some promise for the use of recombinant adeno-associated virus (rAAV)-based gene therapy for the treatment of achromatopsia caused by mutations in the CNGB3 gene. Komaromy et al., Gene therapy rescues cone function in congenital achromatopsia. *Human Molecular Genetics*, 19(13): 2581-2593 (2010) (hereinafter Komaromy et al.). In the canine studies, the rAAV vectors used packaged a human CNGB3 (hCNGB3) expression cassette that contained elements including a 2.1 kb cone red opsin promoter (PR2.1) and a human CNGB3 (hCNGB3) cDNA. One limitation of the studies is that the hCNGB3 driven by the PR2.1 promoter is expressed only in red and green cones, whereas endogenous hCNGB3 is expressed in all three types of cones (red, green and blue cones). Another limitation is that the overall size of the expression cassette utilized (5,230 bp) was well beyond the normal packaging capacity (<4.9 kb) of AAV particles; the over-stuffed rAAV particles dramatically impaired the rAAV packaging efficiency, resulting in low yields, a higher empty-to-full particle ratio, and likely a lower infectivity of the vector. Expression cassettes containing a shorter version of the cone red opsin promoter, or a cone arrestin promoter, were much less effective in restoring visual function. The present invention addresses these limitations.

The present invention has the advantage of providing promoters that are capable of promoting hCNGB3 expression in all three types of cones. In addition, the promoters of the invention have the advantage that they are short enough to make the hCNGB3 expression cassette fit well within the normal packaging capacity of rAAV. A promoter that fits within the normal rAAV packaging capacity provides benefits, such as improved yields, a lower empty-to-full particle ratio, and higher infectivity of the vector. The present invention also provides expression cassettes, vectors and kits that utilize these improved promoters, as well as methods for treating achromatopsia by administering the vectors.

The present invention addresses the need for an effective achromatopsia treatment.

SUMMARY OF THE INVENTION

In one aspect, the instant invention provides an isolated promoter comprising approximately 1.8 kb of the 5'-NTR of the CNGB3 gene. In an exemplary embodiment, the promoter comprises the sequence set forth as SEQ ID NO: 1

In another aspect, the invention provides an isolated promoter comprising approximately 1.6 kb of the 5'-NTR of the CNGB3 gene. In an exemplary embodiment, the promoter comprises the sequence set forth as SEQ ID NO:2

In another aspect, the invention provides an isolated promoter comprising approximately 400 bp of the cytomegalovirus (CMV) enhancer and approximately 1.4 kb of the 5'-NTR of the CNGB3 gene. In an exemplary embodiment, the promoter comprises a cytomegalovirus (CMV) enhancer set forth as SEQ ID NO: 3 and the 5'-NTR of the CNGB3 gene set forth as SEQ ID NO: 4.

In specific embodiments of the invention, the CNGB3 gene is the human CNGB3 gene.

In specific embodiments, the promoters of the invention are capable of promoting CNGB3 expression in S-cone cells, M-cone cells, and L-cone cells.

In other specific embodiments, the promoter is capable of promoting CNGA3 expression in S-cone cells, M-cone cells, and L-cone cells.

In other specific embodiments, the promoter is capable of promoting GNAT2 expression in S-cone cells, M-cone cells, and L-cone cells.

In another aspect, the invention provides a transgene expression cassette comprising a promoter described herein; a nucleic acid selected from the group consisting of a CNGB3 nucleic acid, a CNGA3 nucleic acid, and a GNAT2 nucleic acid; and minimal regulatory elements.

In another aspect, the invention provides a transgene expression cassette comprising a promoter described herein, a CNGB3 nucleic acid, and minimal regulatory elements.

In specific embodiments, the nucleic acid is a human nucleic acid.

In another aspect, the invention provides nucleic acid vectors comprising a expression cassette described herein. In one embodiment, the vector is an adeno-associated viral (AAV) vector. In exemplary embodiments, vectors comprise a serotype of the capsid sequence and a serotype of the ITRs of said AAV vector independently selected from the group consisting of AAV1, AAV2, AAV3, AAV4, AAV5, AAV6, AAV7, AAV8, AAV9, AAV10, AAV11, and AAV12. In another embodiment, the capsid sequence is a mutant capsid sequence.

In another aspect, the invention provides methods for treating a disease associated with a genetic mutation, substitution, or deletion that affects retinal cone cells, wherein the method comprises administering to a subject in need of such treatment a vector that comprises a promoter described herein, thereby treating the subject. In one embodiment, the disease is achromatopsia.

In another aspect, the invention provides methods for treating achromatopsia comprising administering a vector described herein to a subject in need of such treatment, thereby treating the subject. In one embodiment, the vector is administered subretinally.

In another aspect, the invention provides kits comprising a vector that comprises a promoter described herein and instructions for use thereof.

In another embodiment, the invention provides kits comprising a nucleic acid vector described herein, and instructions for use thereof.

In another aspect, the invention provides methods of making a recombinant adeno-associated viral (rAAV) vector comprising inserting into an adeno-associated viral vector described herein and a nucleic acid selected from the group consisting of a CNGB3 nucleic acid, a CNGA3 nucleic acid, and a GNAT2 nucleic acid. In one embodiment, the nucleic acid is a human nucleic acid.

In other embodiments, the serotype of the capsid sequence and the serotype of the ITRs of said AAV vector are independently selected from the group consisting of AAV1, AAV2, AAV3, AAV4, AAV5, AAV6, AAV7, AAV8, AAV9, AAV10, AAV11, and AAV12. In a specific embodiment, the capsid sequence is a mutant capsid sequence.

BRIEF DESCRIPTION OF THE DRAWINGS

FIG. 5 sets for the SEQ ID NOs: 1-4.

DETAILED DESCRIPTION OF THE INVENTION

I. Overview and Definitions

Figure 1:
FIG. 1: Schematic drawing of the truncated human red/green opsin promoter.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

A "subject" or "patient" to be treated by the method of the invention can mean either a human or non-human animal. A "nonhuman animal" includes any vertebrate or invertebrate organism.

"Achromatopsia" is a color vision disorder. Symptoms of achromatopsia include achromatopia (lack of color perception), amblyopia (reduced visual acuity), hemeralopia (reduced visual capacity in bright light accompanied by photoaversion, meaning a dislike or avoidance of bright light), nystagmus (uncontrolled oscillatory movement of the eyes), iris operating abnormalities, and impaired stereovision (inability to perceive three-dimensional aspects of a scene). As used herein, the term "achromatopsia" refers to a form of achromatopsia caused by genetic mutations, substitutions, or deletions.

"Treating" a disease (such as, for example, achromatopsia) means alleviating, preventing, or delaying the occurrence of at least one sign or symptom of the disease.

The asymmetric ends of DNA and RNA strands are called the 5' (five prime) and 3' (three prime) ends, with the 5' end having a terminal phosphate group and the 3' end a terminal hydroxyl group. The five prime (5') end has the fifth carbon in the sugar-ring of the deoxyribose or ribose at its terminus Nucleic acids are synthesized in vivo in the 5'- to 3'-direction, because the polymerase used to assemble new strands attaches each new nucleotide to the 3'-hydroxyl (—OH) group via a phosphodiester bond.

The term "5'-NTR" refers to a region of a gene that is not transcribed into RNA. This region is sometimes also known as the 5'-flanking region, which is generally before or upstream (i.e., toward the 5' end of the DNA) of the transcription initiation site. The 5'-NTR contains the gene promoter and may also contain enhancers or other protein binding sites.

A "promoter" is a region of DNA that facilitates the transcription of a particular gene. As part of the process of transcription, the enzyme that synthesizes RNA, known as RNA polymerase, attaches to the DNA near a gene. Promoters contain specific DNA sequences and response elements that provide an initial binding site for RNA polymerase and for transcription factors that recruit RNA polymerase.

The retina contains three kinds of photoreceptors: rod cells, cone cells, and photoreceptive ganglion cells. Cone cells are of three types: S-cone cells, M-cone cells, and L-cone cells. S-cone cells respond most strongly to short wavelength light (peak near 420-440 nm) and are also known as blue cones. M-cone cells respond most strongly to medium wavelength light (peak near 534-545 nm) and are also known as green cones. L-cone cells respond most strongly to light of long wavelengths (peak near 564-580 nm) and are also known as red cones. The difference in the signals received from the three cone types allows the brain to perceive all possible colors.

A "transgene expression cassette" or "expression cassette" comprises the gene sequences that a nucleic acid vector is to deliver to target cells. These sequences include the gene of interest (e.g., a CNGB3 nucleic acid), one or more promoters, and minimal regulatory elements.

"Minimal regulatory elements" are regulatory elements that are necessary for effective expression of a gene in a target cell and thus should be included in a transgene expression cassette. Such sequences could include, for example, promoter or enhancer sequences, a polylinker sequence facilitating the insertion of a DNA fragment within a plasmid vector, and sequences responsible for intron splicing and polyadenlyation of mRNA transcripts. In a recent example of a gene therapy treatment for achromatopsia, the expression cassette included the minimal regulatory elements of a polyadenylation site, splicing signal sequences, and AAV inverted terminal repeats. See, e.g., Komaromy et al.

A "nucleic acid" or "nucleic acid molecule" is a molecule composed of chains of monomeric nucleotides, such as, for example, DNA molecules (e.g., cDNA or genomic DNA). A nucleic acid may encode, for example, a promoter, the CNGB3 gene or a portion thereof, or regulatory elements. A nucleic acid molecule can be single-stranded or double-stranded. A "CNGB3 nucleic acid" refers to a nucleic acid that comprises the CNGB3 gene or a portion thereof, or a functional variant of the CNGB3 gene or a portion thereof. Similarly, a "CNGA3 nucleic acid" refers to a nucleic acid that comprises the CNGA3 gene or a portion thereof, or a functional variant of the CNGA3 gene or a portion thereof, and a "GNAT2 nucleic acid" refers to a nucleic acid that comprises the GNAT2 gene or a portion thereof, or a functional variant of the GNAT2 gene or a portion thereof. A functional variant of a gene includes a variant of the gene with minor variations such as, for example, silent mutations, single nucleotide polymorphisms, missense mutations, and other mutations or deletions that do not significantly alter gene function.

An "isolated" nucleic acid molecule (such as, for example, an isolated promoter) is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

II. Methods of the Invention

The present invention provides promoters, expression cassettes, vectors, kits, and methods that can be used in the treatment of genetic diseases that affect the cone cells of the retina. Genetic diseases that affect the cone cells of the retina include achromatopsia; Leber congenital amaurosis; cone-rod dystrophy; retinitis pigmentosa, including X-linked retinitis pigmentosa; maculopathies; and age-related macular degeneration. In preferred embodiments, the disease is achromatopsia.

Achromatopsia is a color vision disorder. Autosomal recessive mutations or other types of sequence alterations in three genes are the predominant cause of congenital achromatopsia. See Pang, J.-J. et al. (2010). Achromatopsia as a Potential Candidate for Gene Therapy. In *Advances in Experimental Medicine and Biology*, Volume 664, Part 6, 639-646 (2010). Achromatopsia has been associated with mutations in either the alpha or beta subunits of cyclic nucleotide gated channels (CNGs), which are respectively known as CNGA3 and CNGB3. Mutations in the CNGA3 gene that were associated with achromatopsia are reported in Patel K A, et al. Transmembrane Si mutations in CNGA3 from achromatopsia 2 patients cause loss of function and impaired cellular trafficking of the cone CNG channel. *Invest. Ophthalmol. Vis. Sci.* 46 (7): 2282-90. (2005)., Johnson S, et al. Achromatopsia caused by novel mutations in both CNGA3 and CNGB3. *J. Med. Genet.* 41 (2): e20. (2004)., Wissinger B, et al. CNGA3 mutations in hereditary cone photoreceptor disorders. *Am. J. Hum. Genet.* 69 (4): 722-37. (2001)., and Kohl S, et al. Total colourblindness is caused by mutations in the gene encoding the alpha-subunit of the cone photoreceptor cGMP-gated cation channel. *Nat. Genet.* 19 (3): 257-9. (1998). Mutations in CNGB3 gene that were associated with achromatopsia are reported in Johnson S, et al. Achromatopsia caused by novel mutations in both CNGA3 and CNGB3. *J. Med. Genet.* 41 (2): e20. (2004)., Peng C, et al. Achromatopsia-associated mutation in the human cone photoreceptor cyclic nucleotide-gated channel CNGB3 subunit alters the ligand sensitivity and pore properties of heteromeric channels. *J. Biol. Chem.* 278 (36): 34533-40 (2003)., Bright S R, et al. Disease-associated mutations in CNGB3 produce gain of function alterations in cone cyclic nucleotide-gated channels. *Mol. Vis.* 11: 1141-50 (2005)., Kohl S, et al. CNGB3 mutations account for 50% of all cases with autosomal recessive achromatopsia. *Eur. J. Hum. Genet.* 13 (3): 302-8 (2005)., Rojas C V, et al. A frameshift insertion in the cone cyclic nucleotide gated cation channel causes complete achromatopsia in a consanguineous family from a rural isolate. *Eur. J. Hum. Genet.* 10 (10): 638-42 (2002)., Kohl S, et al. Mutations in the CNGB3 gene encoding the beta-subunit of the cone photoreceptor cGMP-gated channel are responsible for achromatopsia (ACHM3) linked to chromosome 8q21. *Hum. Mol. Genet.* 9 (14): 2107-16 (2000)., Sundin O H, et al. Genetic basis of total colourblindness among the Pingelapese islanders. *Nat. Genet.* 25 (3): 289-93 (2000). Sequence alterations in the gene for cone cell transducin, known as GNAT2, can also cause achromatopsia. See Kohl S, et al., Mutations in the cone photoreceptor G-protein alpha-subunit gene GNAT2 in patients with achromatopsia. Kokl S, et al. Mutations in the cone photoreceptor G-protein alpha-subunit gene GNAT2 in patients with achromatopsia. *Am J Hum Genet* 71 (2):

422-425 (2002) (hereinafter Kohl et al.). The severity of mutations in these proteins correlates with the severity of the achromatopsia phenotype.en.wikipedia.org/wiki/Achromatopsia. Mutations in CNGB3 account for about 50% of cases of achromatopsia. Kohl et al. Mutations in CNGA3 account for about 23% of cases, and mutations in GNAT2 account for about 2% of cases.

The "CNGB3 gene" is the gene that encodes the cyclic nucleotide-gated channel beta 3 (CNGB3). The "CNGA3 gene" is the gene that encodes the cyclic nucleotide-gated channel alpha 3 (CNGA3). The CNGB3 and CNGA3 genes are expressed in cone cells of the retina. Native retinal cyclic nucleotide gated channels (CNGs) are critically involved in phototransduction. CNGs are cation channels that consist of two alpha and two beta subunits. In the dark, cones have a relatively high concentration of cyclic guanosine 3'-5' monophosphate (cGMP), which causes the CNGs to open, resulting in depolarization and continuous glutamate release. Light exposure activates a signal transduction pathway that breaks down cGMP. The reduction in cGMP concentration causes the CNGs to close, preventing the influx of positive ions, hyperpolarizing the cell, and stopping the release of glutamate. Mutations in either the CNGB3 or CNGA3 genes can cause defects in cone photoreceptor function resulting in achromatopsia. Mutations in the CNGB3 gene have been associated with other diseases in addition to achromatopsia, including progressive cone dystrophy and juvenile macular degeneration.

The GNAT2 gene encodes the alpha-2 subunit of guanine nucleotide binding protein, which is also known as the cone-specific alpha transducin. Guanine nucleotide-binding proteins (G proteins) consist of alpha, beta, and gamma subunits. In photoreceptors, G proteins are critical in the amplification and transduction of visual signals. Various types of sequence alterations in GNAT2 can cause human achromatopsia: nonsense mutations, small deletion and/or insertion mutations, frameshift mutations, and large intragenic deletions. Pang et al.

Currently, there is no effective treatment for achromatopsia. Animal studies suggest that it is possible to use gene therapy to treat achromatopsia and other diseases of the retina. For recessive gene defects, the goal is to deliver a wild-type copy of a defective gene to the affected retinal cell type. The ability to deliver genes to some subsets of cone cells was demonstrated, for example, in Mauck, M. C. et al., Longitudinal evaluation of expression of virally delivered transgenes in gerbil cone photoreceptors. *Visual Neuroscience* 25(3): 273-282 (2008). The authors showed that a recombinant AAV vector could be used to achieve long-term expression of a reporter gene encoding green fluorescent protein in specific types of gerbil cone cells. The authors further demonstrated that a human long-wavelength opsin gene could be delivered to specific gerbil cones, resulting in cone responses to long-wavelength light.

Other studies demonstrated that gene therapy with recombinant AAV vectors could be used to convert dichromat monkeys into trichromats by introducing a human L-opsin gene into the squirrel monkey retina. Mancuso, K., et al. Gene therapy for red-green colour blindness in adult primates. *Nature* 461: 784-787 (2009). Electroretinograms verified that the introduced photopigment was functional, and the monkeys showed improved color vision in a behavioral test.

There are several animal models of achromatopsia for which gene therapy experiments have demonstrated the ability to restore cone function. See Pang et al. First, the Gnat2$^{cpfl3}$ mouse has a recessive mutation in the cone-specific alpha transducin gene, resulting in poor visual acuity and little or no cone-specific ERT response. Treatment of homozygous Gnat2$^{cpfl3}$ mice with a single subretinal injection of an AAV serotype 5 vector carrying wild type mouse GNAT2 cDNA and a human red cone opsin promoter restored cone-specific ERG responses and visual acuity. Alexander et al. Restoration of cone vision in a mouse model of achromatopsia. *Nat Med* 13:685-687 (2007) (hereinafter Alexander et al.). Second, the cpfl5 (Cone Photoreceptor Function Loss 5) mouse has an autosomal recessive missense mutation in the CNGA3 gene with no cone-specific ERG response. Treatment of cpfl5 mice with subretinal injection of an AAV vector carrying the wild type mouse CNGA3 gene and a human blue cone promoter (HB570) resulted in restoration of cone-specific ERG responses. Pang et al. Third, there is an Alaskan Malamute dog that has a naturally occurring CNGB3 mutation causing loss of daytime vision and absence of retinal cone function. In this type of dog, subretinal injection of an AAV5 vector containing human CNGB3 cDNA and a human red cone opsin promoter restored cone-specific ERG responses. See, e.g., Komaromy et al.

The prior methods for treatment of achromatopsia using gene therapy were limited by the fact that the promoters used caused expression of transgenes only in certain types of cone cell photoreceptors. The promoters of the present invention can drive gene expression in all three types of cone cells that are present in humans (S-cone cells, M-cone cells, and L-cone cells).

Another limitation of the studies performed by Komaromy et al. was that the overall size of the expression cassette utilized (5,230 bp) was well beyond the normal packaging capacity (<4.9 kb) of AAV particles; the overstuffed rAAV particles dramatically impaired the rAAV packaging efficiency, resulting in low yields, a higher empty-to-full particle ratio, and likely a lower infectivity of the vector. Expression cassettes containing a shorter version of the cone red opsin promoter, or a cone arrestin promoter, were much less effective in restoring visual function. The promoters of the present invention have the advantage that due to their shortened length, they make the hCNGB3 expression cassette efficiently package in an AAV particle. A promoter that fits within the normal rAAV packaging capacity provides benefits, such as improved yields, a lower empty-to-full particle ratio, higher infectivity of the vector, and ultimately, higher efficacy for treatment of the desired condition.

III. Promoters, Expression Cassettes, Nucleic Acids, and Vectors of the Invention The promoters, CNGB3 nucleic acids, regulatory elements, and expression cassettes, and vectors of the invention may be produced using methods known in the art. The methods described below are provided as non-limiting examples of such methods.

Promoters

The present invention provides isolated promoters. In some aspects, these promoters include a segment of the 5'-NTR of the CNGB3 gene. In related aspects, these promoters include a segment of the 5'-NTR of the CNGB3 gene together with one or more enhancer sequences derived from other genes.

In one embodiment, the promoter is an isolated promoter that comprises approximately 1.8 kb of the 5'-NTR of the CNGB3 gene. In a specific embodimentt, the promoter has the sequence SEQ ID NO: 1.

In another embodiment, the promoter is an isolated promoter that comprises approximately 1.6 kb of the 5'-NTR of the CNGB3 gene. In a specific embodiment, the promoter has the sequence SEQ ID NO: 2.

In another embodiment, the invention provides an isolated promoter that comprises (a) an enhancer sequence derived from a gene other than CNGB3 and (b) approximately 1.4 kb of the 5'-NTR of the CNGB3 gene.

In one embodiment, the promoter is an isolated promoter comprising (a) approximately 400 bp of the cytomegalovirus (CMV) enhancer and (b) approximately 1.4 kb of the 5'-NTR of the CNGB3 gene. The cytomegalovirus (CMV) enhancer is an immediate early promoter derived from the cytomegalovirus. It serves to augment transgene expression. In one such embodiment, the promoter comprises the following sequences: (a) [SEQ ID NO: 3] and (b) [SEQ ID NO: 4].

In another embodiment, the promoter is an isolated promoter comprising (a) a promoter sequence selected from the group consisting of a CBA promoter, a Rous sacrcoma virus-RSV promoter, the proximal mouse opsin promoter (mOP), the human G-protein-coupled receptor protein kinase 1 promoter (hGRK1); and (b) approximately 1.4 kb of the 5'-NTR of the CNGB3 gene. The CBA promoter is a fusion of the chicken-actin promoter and CMV immediate-early enhancer, and it allows stable GFP reporter expression in photoreceptor cells after subretinal injections. Dinculescu, A et al., Adeno-associated virus-vector gene therapy for retinal disease. *Human Gene Therapy* 2005; 16:649-663. The RSV promoter has been also been successfully employed to promote in vivo transgene expression in the retina. Lei B et al. Molecular Vision 15:1374-1382 (2009).

In other embodiments, the promoters of the invention that comprise segments of the CNGB3 gene, the CNGB3 gene is a human CNGB3 (hCNGB3) gene. In other embodiments, the CNGB3 gene is a CNGB3 gene from a non-human animal.

In some embodiments of the promoters of the invention, the promoter is capable of promoting expression of a transgene in S-cone, M-cone, and L-cone cells. A "transgene" refers to a segment of DNA containing a gene sequence that has been isolated from one organism and is introduced into a different organism. For example, to treat an individual who has achromatopsia caused by a mutation of the human CNGB3 gene, a wild-type (i.e., non-mutated, or functional variant) human CNGB3 gene may be administered using an appropriate vector. The wild-type gene is referred to as a "transgene." In preferred embodiments, the transgene is a wild-type version of a gene that encodes a protein that is normally expressed in cone cells of the retina. In one such embodiment, the transgene is derived from a human gene. In a first specific embodiment, the promoter is capable of promoting expression of a CNGB3 nucleic acid in S-cone, M-cone, and L-cone cells. In a second specific embodiment, the promoter is capable of promoting expression of a CNGA3 nucleic acid in S-cone, M-cone, and L-cone cells. In a third specific embodiment, the promoter is capable of promoting expression of a GNAT2 nucleic acid in S-cone, M-cone, and L-cone cells. In these three specific embodiments, the CNGB3, CNGA3, or GNAT2 is preferably human CNGB3, CNGA3, or GNAT2.

In another aspect, the present invention provides promoters that are shortened versions of the PR2.1 promoter (see e.g., Example 1), which may optionally include additional enhancer sequences. Such promoters have the advantage that they fit better within the packaging capacity of AAV vectors and therefore provide advantages such as, for example, improved yields, a lower empty-to-full particle ratio, and higher infectivity of the vector. In some embodiments, these promoters are created by truncating the 5'-end of PR2.1 while leaving the 500 bp core promoter and the 600 bp locus control region (LCR) intact. In some such embodiments, the lengths of the truncations are selected from the group consisting of approximately 300 bp, 500 bp, and 1,100 bp (see, e.g., PR1.7, PR1.5, and PR1.1, respectively, as described in Example 1). In one particular embodiment, the present invention provides a shortened promoter that includes a CMV enhancer that is added to the 5'-end of PR1.1. In other embodiments of the present invention, the invention provides promoters that include other types of enhancer sequences, as described supra, that are added to shortened versions of the PR2.1 promoter.

Expression Cassettes

In another aspect, the present invention provides a transgene expression cassette that includes (a) a promoter of the invention; (b) a nucleic acid selected from the group consisting of a CNGB3 nucleic acid, a CNGA3 nucleic acid, and a GNAT2 nucleic acid; and (c) minimal regulatory elements. A promoter of the invention includes the promoters discussed supra.

A "CNGB3 nucleic acid" refers to a nucleic acid that comprises the CNGB3 gene or a portion thereof, or a functional variant of the CNGB3 gene or a portion thereof. Similarly, a "CNGA3 nucleic acid" refers to a nucleic acid that comprises the CNGA3 gene or a portion thereof, or a functional variant of the CNGA3 gene or a portion thereof, and a "GNAT2 nucleic acid" refers to a nucleic acid that comprises the GNAT2 gene or a portion thereof, or a functional variant of the GNAT2 gene or a portion thereof. A functional variant of a gene includes a variant of the gene with minor variations such as, for example, silent mutations, single nucleotide polymorphisms, missense mutations, and other mutations or deletions that do not significantly alter gene function.

In certain embodiments, the nucleic acid is a human nucleic acid (i.e., a nucleic acid that is derived from a human CNGB3, CNGA3, or GNAT2 gene). In other embodiments, the nucleic acid is a non-human nucleic acid (i.e., a nucleic acid that is derived from a non-human CNGB3, CNGA3, or GNAT2 gene).

"Minimal regulatory elements" are regulatory elements that are necessary for effective expression of a gene in a target cell. Such regulatory elements could include, for example, promoter or enhancer sequences, a polylinker sequence facilitating the insertion of a DNA fragment within a plasmid vector, and sequences responsible for intron splicing and polyadenlyation of mRNA transcripts. In a recent example of a gene therapy treatment for achromatopsia, the expression cassette included the minimal regulatory elements of a polyadenylation site, splicing signal sequences, and AAV inverted terminal repeats. See, e.g., Komaromy et al. The expression cassettes of the invention may also optionally include additional regulatory elements that are not necessary for effective incorporation of a gene into a target cell.

Vectors

The present invention also provides vectors that include any one of the expression cassettes discussed in the preceding section. In some embodiments, the vector is an oligonucleotide that comprises the sequences of the expression cassette. In specific embodiments, delivery of the oligonucleotide may be accomplished by in vivo electroporation (see, e.g., Chalberg, T W, et al. phiC31 integrase confers genomic integration and long-term transgene expression in rat retina. *Investigative Ophthalmology & Visual Science*, 46, 2140-2146 (2005) (hereinafter Chalberg et al., 2005)) or electron avalanche transfection (see, e.g., Chalberg, T W, et al. Gene transfer to rabbit retina with electron avalanche transfection. *Investigative Ophthalmology & Visual Science*, 47, 4083-4090 (2006) (hereinafter Chalberg et al., 2006)). In further embodiments, the vector is a DNA-compacting peptide (see, e.g., Farjo, R, et al. Efficient non-viral ocular gene transfer with compacted DNA nanoparticles. *PLoS ONE*, 1, e38 (2006) (hereinafter Farjo et al., 2006), where CK30, a peptide containing a cystein residue coupled to polyethylene glycol followed by 30 lysines, was used for gene transfer to photoreceptors), a peptide with cell penetrating properties (see Johnson, L N, et al., Cell-penetrating peptide for enhanced delivery of nucleic acids and drugs to ocular tissues including retina and cornea. *Molecular Therapy*, 16(1), 107-114 (2007) (hereinafter Johnson et al., 2007), Barnett, E M, et al. Selective cell uptake of modified Tat peptide-fluorophore conjugates in rat retina in ex vivo and in vivo models. *Investigative Ophthalmology & Visual Science*, 47, 2589-2595 (2006) (hereinafter Barnett et al., 2006), Cashman, S M, et al. Evidence of protein transduction but not intercellular transport by proteins fused to HIV tat in retinal cell culture and in vivo. *Molecular Therapy*, 8, 130-142 (2003) (hereinafter Cashman et al., 2003), Schorderet, D F, et al. D-TAT transporter as an ocular peptide delivery system. *Clinical and Experimental Ophthalmology*, 33, 628-635 (2005)(hereinafter Schorderet et al., 2005), Kretz, A, et al. HSV-1 VP22 augments adenoviral gene transfer to CNS neurons in the retina and striatum in vivo. *Molecular Therapy*, 7, 659-669 (2003)(hereinafter Kretz et al. 2003) for examples of peptide delivery to ocular cells), or a DNA-encapsulating lipoplex, polyplex, liposome, or immunoliposome (see e.g., Zhang, Y, et al. Organ-specific gene expression in the rhesus monkey eye following intravenous nonviral gene transfer. *Molecular Vision*, 9, 465-472 (2003) (hereinafter Zhang et al. 2003), Zhu, C, et al. Widespread expression of an exogenous gene in the eye after intravenous administration. *Investigative Ophthalmology & Visual Science*, 43, 3075-3080 (2002) (hereinafter Zhu et al. 2002), Zhu, C., et al. Organ-specific expression of the lacZ gene controlled by the opsin promoter after intravenous gene administration in adult mice. *Journal of Gene Medicine*, 6, 906-912. (2004) (hereinafter Zhu et al. 2004)).

In preferred embodiments, the vector is a viral vector, such as a vector derived from an adeno-associated virus, an adenovirus, a retrovirus, a lentivirus, a vaccinia/poxvirus, or a herpesvirus (e.g., herpes simplex virus (HSV)). See e.g., Howarth. In the most preferred embodiments, the vector is an adeno-associated viral (AAV) vector.

Multiple serotypes of adeno-associated virus (AAV), including 12 human serotypes (AAV1, AAV2, AAV3, AAV4, AAV5, AAV6, AAV7, AAV8, AAV9, AAV10, AAV11, and AAV12) and more than 100 serotypes from nonhuman primates have now been identified. Howarth J L et al., Using viral vectors as gene transfer tools. *Cell Biol Toxicol* 26:1-10 (2010) (hereinafter Howarth et al.). In embodiments of the present invention wherein the vector is an AAV vector, the serotype of the inverted terminal repeats (ITRs) of the AAV vector may be selected from any known human or nonhuman AAV serotype. In preferred embodiments, the serotype of the AAV ITRs of the AAV vector is selected from the group consisting of AAV1, AAV2, AAV3, AAV4, AAV5, AAV6, AAV7, AAV8, AAV9, AAV10, AAV11, and AAV12. Moreover, in embodiments of the present invention wherein the vector is an AAV vector, the serotype of the capsid sequence of the AAV vector may be selected from any known human or animal AAV serotype. In some embodiments, the serotype of the capsid sequence of the AAV vector is selected from the group consisting of AAV1, AAV2, AAV3, AAV4, AAV5, AAV6, AAV7, AAV8, AAV9, AAV10, AAV11, and AAV12. In preferred embodiments, the serotype of the capsid sequence is AAV5. In some embodiments wherein the vector is an AAV vector, a pseudotyping approach is employed, wherein the genome of one ITR serotype is packaged into a different serotype capsid. See e.g., Zolutuhkin S. et al. Production and purification of serotype 1, 2, and 5 recombinant adeno-associated viral vectors. *Methods* 28(2): 158-67 (2002). In preferred embodiments, the serotype of the AAV ITRs of the AAV vector and the serotype of the capsid sequence of the AAV vector are independently selected from the group consisting of AAV1, AAV2, AAV3, AAV4, AAV5, AAV6, AAV7, AAV8, AAV9, AAV10, AAV11, and AAV12.

In some embodiments of the present invention wherein the vector is a rAAV vector, a mutant capsid sequence is employed. Mutant capsid sequences, as well as other techniques such as rational mutagenesis, engineering of targeting peptides, generation of chimeric particles, library and directed evolution approaches, and immune evasion modifications, may be employed in the present invention to optimize AAV vectors, for purposes such as achieving immune evasion and enhanced therapeutic output. See e.g., Mitchell A. M. et al. AAV's anatomy: Roadmap for optimizing vectors for translational success. *Curr Gene Ther.* 10(5): 319-340.

Making the Nucleic Acids of the Invention

A nucleic acid molecule (including, for example, a promoter, CNGB3 nucleic acid, CNGA3 nucleic acid, a GNAT2 nucleic acid, or a regulatory element) of the present invention can be isolated using standard molecular biology techniques. Using all or a portion of a nucleic acid sequence of interest as a hybridization probe, nucleic acid molecules can be isolated using standard hybridization and cloning techniques (e.g., as described in Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989).

A nucleic acid molecule for use in the methods of the invention can also be isolated by the polymerase chain reaction (PCR) using synthetic oligonucleotide primers designed based upon the sequence of a nucleic acid molecule of interest. A nucleic acid molecule used in the methods of the invention can be amplified using cDNA, mRNA or, alternatively, genomic DNA as a template and appropriate oligonucleotide primers according to standard PCR amplification techniques.

Furthermore, oligonucleotides corresponding to nucleotide sequences of interest can also be chemically synthesized using standard techniques. Numerous methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373, 071, incorporated by reference herein). Automated methods for designing synthetic oligonucleotides are available. See e.g., Hoover, D. M. & Lubowski, J. *Nucleic Acids Research*, 30(10): e43 (2002).

Many embodiments of the invention involve a CNGB3 nucleic acid, a CNGA3 nucleic acid, or a GNAT2 nucleic acid. Some aspects and embodiments of the invention involve other nucleic acids, such as isolated promoters or regulatory elements. A nucleic acid may be, for example, a cDNA or a chemically synthesized nucleic acid. A cDNA can be obtained, for example, by amplification using the polymerase chain reaction (PCR) or by screening an appropriate cDNA library. Alternatively, a nucleic acid may be chemically synthesized.

IV. Methods and Kits of the Invention

Methods of Treatment

The invention provides methods for treating a disease associated with a genetic mutation, substitution, or deletion that affects retinal cone cells, wherein the methods comprise administering to a subject in need of such treatment a vector that includes one of the promoters of the invention, thereby treating the subject. In one embodiment, the disease affects the retinal pigment epithelium (PRE). In a specific embodiment, the disease is achromatopsia. Other diseases associated with a genetic mutation, substitution, or deletion that affects retinal cone cells include achromatopsia, Leber congenital amaurosis, cone-rod dystrophy, maculopathies, age-related macular degeneration and retinitis pigmentosa, including X-linked retinitis pigmentosa.

The invention further provides methods for treating achromatopsia comprising administering any of the vectors of the invention to a subject in need of such treatment, thereby treating the subject.

A "subject" to be treated by the methods of the invention can mean either a human or non-human animal. A "nonhuman animal" includes any vertebrate or invertebrate organism. In some embodiments, the nonhuman animal is an animal model of retinal disease, or of achromatopsia in particular. See e.g., Pang et al., Alexander et al., Komaromy et al. Various large animal models are available for the study of AAV-mediated gene-based therapies in the retina. Stieger K. et al. AAV-mediated gene therapy for retinal disorders inlarge animal models. ILAR J. 50(2): 206-224 (2009). The promoters of the invention are described supra. "Treating" a disease (such as, for example, achromatopsia) means alleviating, preventing, or delaying the occurrence of at least one sign or symptom of the disease. A "sign" of a disease is a manifestation of the disease that can be observed by others or measured by objective methods, such as, e.g., electroretinography or behavioral testing. A "symptom" of a disease is a characteristic of the disease that is subjectively perceived by the subject.

In either of these two methods of treatment, the vector can be any type of vector known in the art. In some embodiments, the vector is a non-viral vector, such as a naked DNA plasmid, an oligonucleotide (such as, e.g., an antisense oligonucleotide, a small molecule RNA (siRNA), a double stranded oligodeoxynucleotide, or a single stranded DNA oligonucleotide). In specific embodiments involving oligonucleotide vectors, delivery may be accomplished by in vivo electroporation (see e.g., Chalberg et al., 2005) or electron avalanche transfection (see e.g., Chalberg et al. 2006). In further embodiments, the vector is a dendrimer/DNA complex that may optionally be encapsulated in a water soluble polymer, a DNA-compacting peptide (see e.g., Farjo et al. 2006, where CK30, a peptide containing a cystein residue coupled to poly ethylene glycol followed by 30 lysines, was used for gene transfer to photoreceptors), a peptide with cell penetrating properties (see Johnson et al. 2007; Barnett et al., 2006; Cashman et al., 2003; Schorderet et al., 2005; Kretz et al. 2003 for examples of peptide delivery to ocular cells), or a DNA-encapsulating lipoplex, polyplex, liposome, or immunoliposome (see e.g., Zhang et al. 2003; Zhu et al. 2002; Zhu et al. 2004). In many additional embodiments, the vector is a viral vector, such as a vector derived from an adeno-associated virus, an adenovirus, a retrovirus, a lentivirus, a vaccinia/poxvirus, or a herpesvirus (e.g., herpes simplex virus (HSV)). See e.g., Howarth. In preferred embodiments, the vector is an adeno-associated viral (AAV) vector.

In the methods of treatment of the present invention, administering of a vector can be accomplished by any means known in the art. In preferred embodiments, the administration is by subretinal injection. In certain embodiments, the subretinal injection is delivered preferentially to one or more regions where cone density is particularly high (such as e.g., the tapetal zone superior to the optic disc). In other embodiments, the administration is by intraocular injection, intravitreal injection, or intravenous injection. Administration of a vector to the retina may be unilateral or bilateral and may be accomplished with or without the use of general anesthesia.

In the methods of treatment of the present invention, the volume of vector delivered may be determined based on the characteristics of the subject receiving the treatment, such as the age of the subject and the volume of the area to which the vector is to be delivered. It is known that eye size and the volume of the subretinal space differ among individuals and may change with the age of the subject. In embodiments wherein the vector is administered subretinally, vector volumes may be chosen with the aim of covering all or a certain percentage of the subretinal space, or so that a particular number of vector genomes is delivered.

In the methods of treatment of the present invention, the concentration of vector that is administered may differ depending on production method and may be chosen or optimized based on concentrations determined to be therapeutically effective for the particular route of administration. In some embodiments, the concentration in vector genomes per milliliter (vg/ml) is selected from the group consisting of about $10^8$ vg/ml, about $10^9$ vg/ml, about $10^{10}$ vg/ml, about $10^{11}$ vg/ml, about $10^{12}$ vg/ml, about $10^{13}$ vg/ml, and about $10^{14}$ vg/ml. In preferred embodiments, the concentration is in the range of $10^{10}$ vg/ml-$10^{13}$ vg/ml delivered by subretinal injection or intravitreal injection in a volume of about 0.1 mL, about 0.2 mL, about 0.4 mL, about 0.6 mL, about 0.8 mL, and about 1.0 mL Kits The present invention also provides kits. In one aspect, a kit of the invention comprises a vector that comprises (a) any one of the promoters of the invention and (b) instructions for use thereof. In another aspect, a kit of the invention comprises (a) any one of the vectors of the invention, and (b) instructions for use thereof. The promoters and vectors of the invention are described supra. In some embodiments, a vector of the invention may be any type of vector known in the art, including a non-viral or viral vector, as described supra. In preferred embodiments, the vector is a viral vector, such as a vector derived from an adeno-associated virus, an adenovirus, a retrovirus, a lentivirus, a vaccinia/poxvirus, or a herpesvirus (e.g., herpes simplex virus (HSV)). In the most preferred embodiments, the vector is an adeno-associated viral (AAV) vector.

The instructions provided with the kit may describe how the promoter can be incorporated into a vector or how the vector can be administered for therapeutic purposes, e.g., for treating a disease associated with a genetic mutation, substitution, or deletion that affects retinal cone cells. In some embodiments wherein the kit is to be used for therapeutic purposes, the instructions include details regarding recommended dosages and routes of administration.

Methods of Making Recombinant Adeno-Associated Viral Vectors (AAV Vectors)

The present invention also provides methods of making a recombinant adeno-associated viral (rAAV) vector comprising inserting into an adeno-associated viral vector any one of the promoters of the invention (described supra) and a nucleic acid selected from the group consisting of a CNGB3 nucleic acid, a CNGA3 nucleic acid, and a GNAT2 nucleic acid (also described supra). In some embodiments, the nucleic acid is a human nucleic acid, i.e., a nucleic acid derived from a human CNGB3, CNGA or GNAT gene, or a functional variant thereof. In alternative embodiments, the nucleic acid is a nucleic acid derived from a non-human gene.

In the methods of making an rAAV vector that are provided by the invention, the serotype of the capsid sequence and the serotype of the ITRs of said AAV vector are independently selected from the group consisting of AAV1, AAV2, AAV3, AAV4, AAV5, AAV6, AAV7, AAV8, AAV9, AAV10, AAV11, and AAV12. Thus, the invention encompasses vectors that use a pseudotyping approach, wherein the genome of one ITR serotype is packaged into a different serotype capsid. See e.g., Daya S. and Berns, K. I., Gene therapy using adeno-associated virus vectors. *Clinical Microbiology Reviews,* 21(4): 583-593 (2008) (hereinafter Daya et al.). Furthermore, in some embodiments, the capsid sequence is a mutant capsid sequence.

AAV Vectors

AAV vectors are derived from adeno-associated virus, which has its name because it was originally described as a contaminant of adenovirus preparations. AAV vectors offer numerous well-known advantages over other types of vectors: wildtype strains infect humans and nonhuman primates without evidence of disease or adverse effects; the AAV capsid displays very low immunogenicity combined with high chemical and physical stability which permits rigorous methods of virus purification and concentration; AAV vector transduction leads to sustained transgene expression in postmitotic, nondividing cells and provides long-term gain of function; and the variety of AAV subtypes and variants offers the possibility to target selected tissues and cell types. Heilbronn R & Weger S, Viral Vectors for Gene Transfer: Current Status of Gene Therapeutics, in M. Schäfer-Korting (ed.), *Drug Delivery*, Handbook of Experimental Pharmacology, 197: 143-170 (2010) (hereinafter Heilbronn). A major limitation of AAV vectors is that the AAV offers only a limited transgene capacity (<4.9 kb) for a conventional vector containing single-stranded DNA.

AAV is a nonenveloped, small, single-stranded DNA-containing virus encapsidated by an icosahedral, 20 nm diameter capsid. The human serotype AAV2 was used in a majority of early studies of AAV. Heilbronn. It contains a 4.7 kb linear, single-stranded DNA genome with two open reading frames rep and cap ("rep" for replication and "cap" for capsid). Rep codes for four overlapping nonstructural proteins: Rep78, Rep68, Rep52, and Rep40. Rep78 and Rep69 are required for most steps of the AAV life cycle, including the initiation of AAV DNA replication at the hairpin-structured inverted terminal repeats (ITRs), which is an essential step for AAV vector production. The cap gene codes for three capsid proteins, VP1, VP2, and VP3. Rep and cap are flanked by 145 bp ITRs. The ITRs contain the origins of DNA replication and the packaging signals, and they serve to mediate chromosomal integration. The ITRs are generally the only AAV elements maintained in AAV vector construction.

To achieve replication, AAVs must be coinfected into the target cell with a helper virus. Grieger J C & Samulski R J, Adeno-associated virus as a gene therapy vector: Vector development, production, and clinical applications. *Adv Biochem Engin/Biotechnol* 99:119-145 (2005). Typically, helper viruses are either adenovirus (Ad) or herpes simplex virus (HSV). In the absence of a helper virus, AAV can establish a latent infection by integrating into a site on human chromosome 19. Ad or HSV infection of cells latently infected with AAV will rescue the integrated genome and begin a productive infection. The four Ad proteins required for helper function are E1A, E1B, E4, and E2A. In addition, synthesis of Ad virus-associated (VA) RNAs is required. Herpes viruses can also serve as helper viruses for productive AAV replication. Genes encoding the helicase-primase complex (UL5, UL8, and UL52) and the DNA-binding protein (UL29) have been found sufficient to mediate the HSV helper effect. In some embodiments of the present invention that employ rAAV vectors, the helper virus is an adenovirus. In other embodiments that employ rAAV vectors, the helper virus is HSV.

Making Recombinant AAV (rAAV) Vectors

The production, purification, and characterization of the rAAV vectors of the present invention may be carried out using any of the many methods known in the art. For reviews of laboratory-scale production methods, see, e.g., Clark R K, Recent advances in recombinant adeno-associated virus vector production. *Kidney Int.* 61s:9-15 (2002); Choi V W et al., Production of recombinant adeno-associated viral vectors for in vitro and in vivo use. *Current Protocols in Molecular Biology* 16.25.1-16.25.24 (2007) (hereinafter Choi et al.); Grieger J C & Samulski R J, Adeno-associated virus as a gene therapy vector: Vector development, production, and clinical applications. *Adv Biochem Engin/Biotechnol* 99:119-145 (2005) (hereinafter Grieger & Samulski); Heilbronn R & Weger S, Viral Vectors for Gene Transfer: Current Status of Gene Therapeutics, in M. Schäfer-Korting (ed.), *Drug Delivery*, Handbook of Experimental Pharmacology, 197: 143-170 (2010) (hereinafter Heilbronn); Howarth J L et al., Using viral vectors as gene transfer tools. *Cell Biol Toxicol* 26:1-10 (2010) (hereinafter Howarth). The production methods described below are intended as non-limiting examples.

AAV vector production may be accomplished by cotransfection of packaging plasmids. Heilbronn. The cell line supplies the deleted AAV genes rep and cap and the required helpervirus functions. The adenovirus helper genes, VA-RNA, E2A and E4 are transfected together with the AAV rep and cap genes, either on two separate plasmids or on a single helper construct. A recombinant AAV vector plasmid wherein the AAV capsid genes are replaced with a transgene expression cassette (comprising the gene of interest, e.g., a CNGB3 nucleic acid; a promoter; and minimal regulatory elements) bracketed by ITRs, is also transfected. These packaging plasmids are typically transfected into 293 cells, a human cell line that constitutively expresses the remaining required Ad helper genes, E1A and E1B. This leads to amplification and packaging of the AAV vector carrying the gene of interest.

Multiple serotypes of AAV, including 12 human serotypes and more than 100 serotypes from nonhuman primates have now been identified. Howarth et al. The AAV vectors of the present invention may comprise capsid sequences derived from AAVs of any known serotype. As used herein, a "known serotype" encompasses capsid mutants that can be produced using methods known in the art. Such methods, include, for example, genetic manipulation of the viral capsid sequence, domain swapping of exposed surfaces of the capsid regions of different serotypes, and generation of AAV chimeras using techniques such as marker rescue. See Bowles et al. Marker rescue of adeno-associated virus (AAV) capsid mutants: A novel approach for chimeric AAV production. Journal of Virology, 77(1): 423-432 (2003), as well as references cited therein. Moreover, the AAV vectors of the present invention may comprise ITRs derived from AAVs of any known serotype. Preferentially, the ITRs are derived from one of the human serotypes AAV1-AAV12. In some embodiments of the present invention, a pseudotyping approach is employed, wherein the genome of one ITR serotype is packaged into a different serotype capsid.

Preferentially, the capsid sequences employed in the present invention are derived from one of the human serotypes AAV1-AAV12. Recombinant AAV vectors containing an AAV5 serotype capsid sequence have been demonstrated to target retinal cells in vivo. See, for example, Komaromy et al. Therefore, in preferred embodiments of the present invention, the serotype of the capsid sequence of the AAV vector is AAV5. In other embodiments, the serotype of the capsid sequence of the AAV vector is AAV1, AAV2, AAV3, AAV4, AAV6, AAV7, AAV8, AAV9, AAV10, AAV11, or AAV12. Even when the serotype of the capsid sequence does not naturally target retinal cells, other methods of specific tissue targeting may be employed. See Howarth et al. For example, recombinant AAV vectors can be directly targeted by genetic manipulation of the viral capsid sequence, particularly in the looped out region of the AAV three-dimensional structure, or by domain swapping of exposed surfaces of the capsid regions of different serotypes, or by generation of AAV chimeras using techniques such as marker rescue. See Bowles et al. Marker rescue of adeno-associated virus (AAV) capsid mutants: A novel approach for chimeric AAV production. Journal of Virology, 77(1): 423-432 (2003), as well as references cited therein.

One possible protocol for the production, purification, and characterization of recombinant AAV (rAAV) vectors is provided in Choi et al. Generally, the following steps are involved: design a transgene expression cassette, design a capsid sequence for targeting a specific receptor, generate adenovirus-free rAAV vectors, purify and titer. These steps are summarized below and described in detail in Choi et al.

The transgene expression cassette may be a single-stranded AAV (ssAAV) vector or a "dimeric" or self-complementary AAV (scAAV) vector that is packaged as a pseudo-double-stranded transgene. Choi et al.; Heilbronn; Howarth. Using a traditional ssAAV vector generally results in a slow onset of gene expression (from days to weeks until a plateau of transgene expression is reached) due to the required conversion of single-stranded AAV DNA into double-stranded DNA. In contrast, scAAV vectors show an onset of gene expression within hours that plateaus within days after transduction of quiescent cells. Heilbronn. However, the packaging capacity of scAAV vectors is approximately half that of traditional ssAAV vectors. Choi et al. Alternatively, the transgene expression cassette may be split between two AAV vectors, which allows delivery of a longer construct. See e.g., Daya et al. A ssAAV vector can be constructed by digesting an appropriate plasmid (such as, for example, a plasmid containing the hCNGB3 gene) with restriction endonucleases to remove the rep and cap fragments, and gel purifying the plasmid backbone containing the AAVwt-ITRs. Choi et al. Subsequently, the desired transgene expression cassette can be inserted between the appropriate restriction sites to construct the single-stranded rAAV vector plasmid. A scAAV vector can be constructed as described in Choi et al.

Then, a large-scale plasmid preparation (at least 1 mg) of the pTR proviral plasmids and the suitable AAV helper plasmid and pXX6 Ad helper plasmid can be purified by double CsCl gradient fractionation. Choi et al. A suitable AAV helper plasmid may be selected from the pXR series, pXR1-pXR5, which respectively permit cross-packaging of AAV2 ITR genomes into capsids of AAV serotypes 1 to 5. The appropriate capsid may be chosen based on the efficiency of the capsid's targeting of the cells of interest. For example, in a preferred embodiment of the present invention, the serotype of the capsid sequence of the rAAV vector is AAV5, because this type of capsid is known to effectively target retinal cells. Known methods of varying genome (i.e., transgene expression cassette) length and AAV capsids may be employed to improve expression and/or gene transfer to specific cell types (e.g., retinal cone cells). See, e.g., Yang G S, Virus-mediated transduction of murine retina with adeno-associated virus: Effects of viral capsid and genome size. Journal of Virology, 76(15): 7651-7660.

Next, 293 cells are transfected with pXX6 helper plasmid, rAAV vector plasmid, and AAV helper plasmid. Choi et al. Subsequently the fractionated cell lysates are subjected to a multistep process of rAAV purification, followed by either CsCl gradient purification or heparin sepharose column purification. The production and quantitation of rAAV virions may be determined using a dot-blot assay. In vitro transduction of rAAV in cell culture can be used to verify the infectivity of the virus and functionality of the expression cassette.

In addition to the methods described in Choi et al, various other transfection methods for production of AAV may be used in the context of the present invention. For example, transient transfection methods are available, including methods that rely on a calcium phosphate precipitation protocol.

In addition to the laboratory-scale methods for producing rAAV vectors, the present invention may utilize techniques known in the art for bioreactor-scale manufacturing of AAV vectors, including, for example, Heilbronn; Clement, N. et al. Large-scale adeno-associated viral vector production using a herpesvirus-based system enables manufacturing for clinical studies. Human Gene Therapy, 20: 796-606.

The present invention is further illustrated by the following examples, which should not be construed as further limiting. The contents of all figures and all references, patents and published patent applications cited throughout this application, as well as the Figures, are expressly incorporated herein by reference in their entirety.

EXAMPLES

Example 1

Creation and Testing of Shorter Versions of the PR2.1 Promoter

Prior investigators created a truncated human red/green cone opsin promoter based on the locations of six different deletions found in blue cone monochromats (0.6 to 55 kb). Wang, Y., et al. A locus control region adjacent to the human red and green pigment genes. *Neuron* 9: 429-440 (1992); Nathans, J., et al. Molecular genetics of human blue cone monochromacy. *Science* 245: 831-838 (1989); Shaaban, S. et al. Functional analysis of the promoters of the human red and green visual pigment genes; *Integrative Opthalmology*

& *Visual Science:* 39(6): 885-896 (1998). This truncated red/green opsin promoter is shown in FIG. 1.

Figure 2:
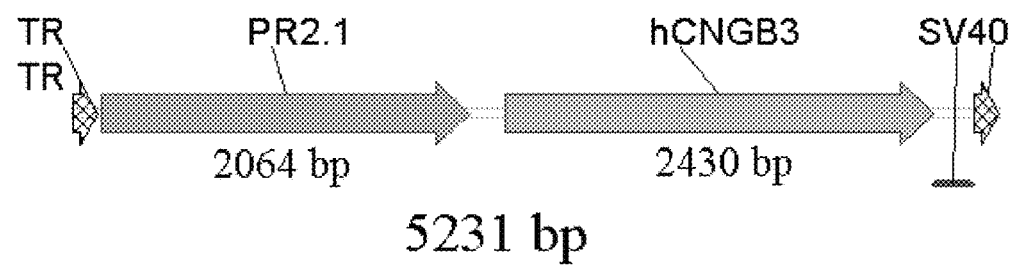
FIG. 2: Schematic drawing of the rAAV5-PR2.1-hCNGB3 vector.

In Komaromy et al. a recombinant adeno associated viral (rAAV) vector was utilized, as shown in FIG. 2. This vector was derived from a human adeno-associated virus of serotype 5 and thus contained the capsid sequences of AAV5. It packaged an expression cassette that contained the PR2.1 cone red opsin promoter (PR2.1) of 2064 bp and a human CNGB3 (hCNGB3) sequence of 2430 bp. In addition, the expression cassette contained SV40 poly(A) and splicing signal sequences, flanked by AAV2 inverted terminal repeats (ITRs). The total size of the expression cassette was 5231 bp, which is well beyond the normal packaging capacity of an AAV vector. In two production runs, it was found that the yield of rAAV5-PR2.1-hCNGB3 was approximately 3- to 5-fold lower when compared to production runs of rAAV1-hAAT that packages a hAAT expression cassette of 3843 bp, which is much smaller that that of the hCNGB3 expression cassette (5231 bp). Also, a higher empty-to-full particle ratio was observed using silver staining and electron microscopy (EM) when compared to rAAV1-hAAT that was manufactured using the same HSV complementation system. Another limitation of the PR2.1 promoter is that it promotes expression of the hCNGB3 transgene in red/green cones with little expression in blue cones.

In the present experiments, shortened versions of the PR2.1 promoter were created and tested.

Materials and Methods

Figure 3:
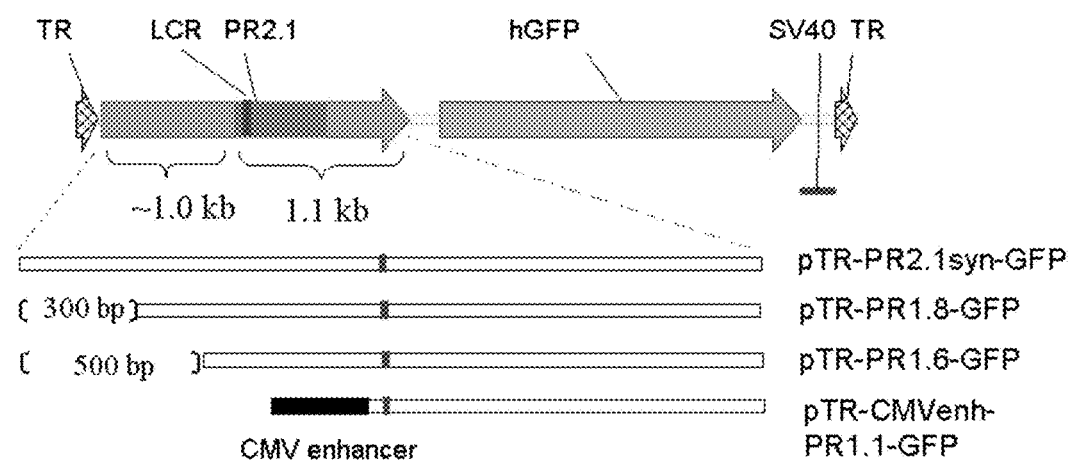
FIG. 3: Schematic drawings of four proviral plasmids that contain variants of the PR2.1 promoter. The PR2.1 promoter (a truncated human red/green opsin promoter) was truncated at its 5'-end by 300 bp, 500 bp, and 1,100 bp to create shorter promoters, designated PR1.7, PR1.5, and PR1.1, respectively. A CMV enhancer was added to the 5' end of the PR1.1 to create a hybrid promoter. The 500 bp core promoter (shown in gray) and the locus control region (shown in red) of PR2.1 were left intact in each of these constructs. Terminal repeats are indicated by the arrows, and the location of SV40 splicing signal sequences is shown.
Figure 4:
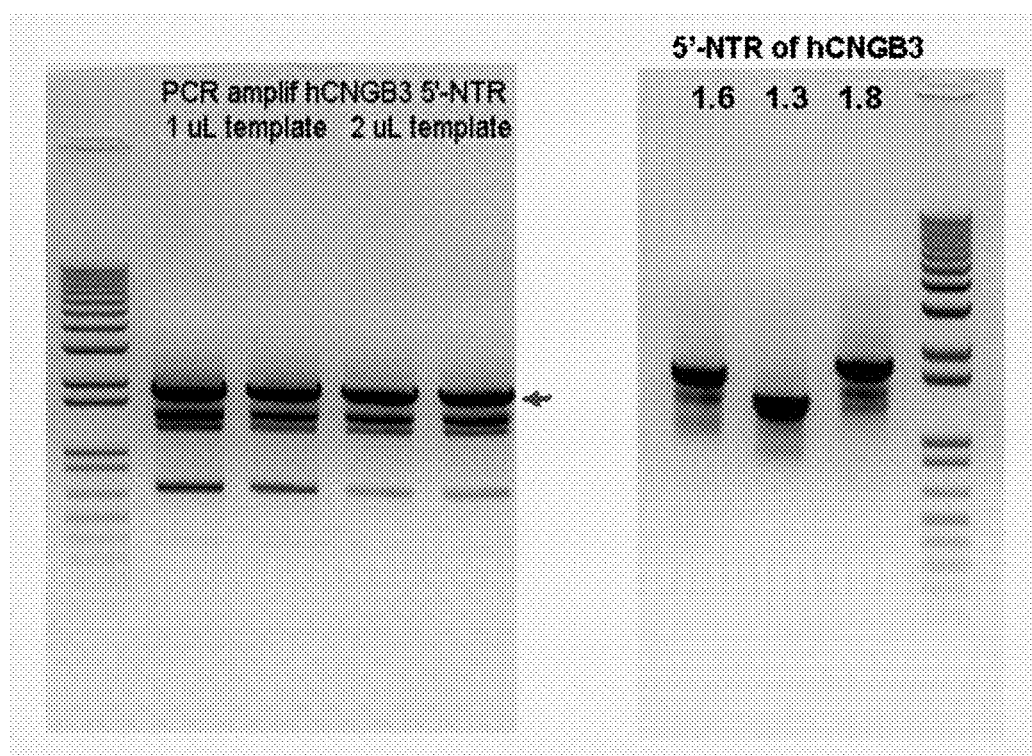
FIG. 4: 5'-NTR sequences of different lengths were PCR amplified from the hCNGB3 gene.

The PR2.1 promoter was shortened by making truncations starting from the 5'-end of PR2.1. The 500 bp core promoter and the 600 bp locus control region (LCR) of PR2.1 were left intact. Three shortened versions of the PR2.1 promoter were created: PR1.7, PR1.5, and PR1.1. These were respectively created by truncating PR2.1 at the 5'-end by approximately 300 bp, 500 bp, and 1,100 bp. A CMV enhancer was added to the 5' end of the PR1.1 to create a hybrid promoter. Proviral plasmids that contained each of these promoters were created, as shown in FIG. 3. These proviral plasmids (p) contained AAV terminal repeats (TR), a synthesized promoter (PR2.1-syn) or truncations thereof, with or without a CMV enhancer (CMVenh), and a green fluorescent protein (GFP) transgene. The following four proviral plasmids were constructed and sequenced:
(1) pTR-PR2.1syn-GFP
(2) pTR-PR1.8-GFP
(3) pTR-PR1.6-GFP
(4) pTR-CMVenh-PR1.1-GFP.

To construct pTR-PR2.1syn-GFP, a parental plasmid pTR-CMVenh-hGFP was first constructed from pTR-CBA-hRS1 by replacing the CBA and hRS1 sequences with enh-hGFP sequences. The human GFP (hGFP) DNA sequence was PCR amplified from pTR-CBA-hGFP, a plasmid containing hGFP open reading frame, with oligonucleotide primers with endonuclease restriction sites at both ends (Not I and BspHI), digested with Not I/BspHI, and joined into pTR-CBA-hRS1 plasmid that had been digested with NotI/NcoI to remove all unnecessary DNA sequences including the chicken beta actin promoter and the hRS1 (but not the CMV enhancer). The resulting plasmid pTR-CMVenh-hGFP contains the CMV enhancer, the hGFP open reading frame (ORF), and the SV40 poly (A) sequence flanked by AAV2 ITRs. The PR2.1 DNA sequence was synthesized according to the DNA sequence 5' of the human red cone opsin (Wang Y. et al., A locus control region adjacent to the human red and green visual pigment genes, Neuron, vol 9, pp 429-440, 1992). The synthesized PR2.1 was composed of bases spanning −4564 to −3009 joined to bases −496 to 0 and contained a LCR essential for expression of both the L and M opsin genes in humans (Komaromy A M et al., Targeting gene expression to cones with human cone opsin promoters in recombinant AAV, Gene Therapy, vol 15, pp 1049-1055, 2008). In addition, a 97 base pair SV40 splice donor/splice acceptor (SD/SA) was attached to the end of PR2.1 promoter. Synthesized PR2.1 including the SD/SA sequence was inserted into the pJ206 cloning vector to generate pJ206-PR2.1syn. The PR2.1syn DNA sequence, including the SV40 SD/SA sequence, was released from pJ206-PR2.1syn by HindIII/Acc65I digestion and inserted into pTR-CMVenh-hGFP that had been digested with HindIII/Acc65I to remove the unnecessary CMV enhancer sequence to generate the plasmid pTR-PR2.1syn-hGFP.

To construct plasmids with shorter versions of the PR2.1 promoter, the PR2.1 sequence with truncation of 300 bp, 500 bp or 1,100 bp from the 5' end of PR2.1 were PCR amplified from pJ206-PR2.1syn. Four oligonucleotide primers were designed:
1) PR right-Hind: 5'-GATTTAAGCTTGCGGCCGCGGG-TACAATTCCGCAGCTTTTAGAG-3' (SEQ ID No: 5);
2) PR1.1 Left-Hind: 5'-CTGCAAGCTTGTGGGACCA-CAAATCAG-3' (SEQ ID NO: 6);
3) PR1.5 Left-Acc65I: 5'-TAGCGGTACCAGCCATCG-GCTGTTAG-3' (SEQ ID NO: 7); and
4) PR1.7 left-Acc65I: 5'-GTGGGTACCGGAGGCT-GAGGGGTG-3' (SEQ ID NO: 8). Primer PR right-Hind was paired with the other three primers to PCR amplify PR1.1, PR1.5, and PR1.7 respectively. Pfu Ultra HS polymerase mix was used with a thermal cycle of 95° C. for 5 min, and then 35 cycles of 94° C. for 1 min, 58° C. for 45 sec, and 72° C. for 2 min.

DNA was amplified from pTR-CMVenh-PR1.1-hGFP: PR1.1 using the primer set of PR right-Hind and PR1.1-left-Hind. The amplified DNA was digested with HindIII and inserted into pTR-CMVenh-hGFP that had been digested with HindIII to generate plasmid pTR-CMVenh-PR1.1-hGFP.

DNA was amplified from pTR-PR1.5-hGFP: PR1.5 using the primer set of PR right-Hind and PR1.5-left-Acc65I. The amplified DNA was digested with HindIII/Acc65I, and inserted into pTR-CMVenh-hGFP that had been digested with HindIII/Acc65I to generate plasmid pTR-PR1.5-hGFP DNA was amplified from pTR-PR1.7-hGFP: PR1.7 using the primer set of PR right-Hind and PR1.7-left-Acc65I. The amplified DNA was digested with HindIII/Acc65I, and inserted into pTR-CMVenh-hGFP that had been digested with HindIII/Acc65I to generate plasmid pTR-PR1.7-hGFP.

The DNA sequence of the expression cassette, including the promoter and hGFP, were confirmed by DNA sequencing, and the location of TRs was confirmed by SmaI restriction mapping.

To examine if the PR2.1 promoter is functional for RNA transcription and subsequent protein expression, a human retinal pigment epithelia (RPE) cell line, APRE-19, and human embryonic kidney HEK293 cells were seeded in 6-well plates ($5\times10^5$ cells/well) and then transfected with 1 μg of DNA from each of six plasmids: pTR-CMVenh-PR1.1-GFP, pTR-PR1.5-GFP, pTR-PR1.7-GFP, pTR-PR2.1syn-GFP, pTR-PR2.1-GFP (Control), or pTR-sm-CBA-GFP (positive control). Transfected cells were incubated at 37° C., 5% $CO_2$ incubator for 4 days. During the period of incubation, transfected cells were examined by fluorescence microscopy for GFP expression.

Results

DNA sequencing and restriction mapping of all four plasmids confirmed that the sequence and the TRs of these proviral plasmids are correct.

In vitro analysis using ARPE-19 and HEK293 cells found that neither of these cell lines supported functionality of the PR2.1 promoter. At 24 h post transfection, strong GFP-expression was observed in cells transfected with DNA from pTR-smCBA-GFP (positive control). At 48 h post transfection, weak GFP expression was observed in cells transfected with DNA from pTR-CMVenh-PR1.1-GFP. No GFP-expressing cells were observed in all other wells, i.e. those transfected with DNA from pTR-PR1.5-GFP, pTR-PR1.7-GFP, pTR-PR2.1syn-GFP, or pTR-PR2.1-GFP. Plasmid pTR-PR2.1-GFP contains the full-length PR2.1 promoter that is known to be functional for RNA transcription and subsequent GFP expression in vivo (Komaromy A M et al., Targeting gene expression to cones with human cone opsin promoters in recombinant AAV, Gene Therapy, vol 15, pp 1049-1055, 2008). Therefore these results indicate that the ARPE-19 cell line does not support PR2.1 promotor, neither any other shorter versions of PR2.1 promoter. Weak expression of GFP from pTR-CMVenh-PR1.1-GFP transfected cells is most likely due to the CMV enhancer, which greatly elevates the strength of the PR1.1 promoter.

In follow-up experiments, the new constructs will be packaged in a rAAV capsid and tested in vivo in a mouse model. Five rAAV vectors, i.e. rAAV5-CMVenh-PR1.1-GFP, rAAV5-PR1.5-GFP, rAAV5-PR1.7-GFP, rAAV5-PR2.1syn-GFP, and rAAV5-PR2.1-GFP, will be produced by a standard plasmid transfection method. The rAAV vectors that have been packaged in transfected cells will be harvested by cell lysis and then purified by iodixanol (IDX) gradient followed by Q Sepharose HP column chromatography, and formulated in Alcon BSS solution. Normal mice will then be injected by subretinal injection (1 µL) in both eyes (5 mice per vector). Six weeks post injection, mice will be sacrificed, eyes enucleated and retinal sections prepared. Slides will be stained with DAPI to identify nuclei and immunostained for GFP and for PNA (a marker for cone photoreceptors). The slides will be evaluated for quantitative GFP expression and localization of GFP expression in cones.

Example 2

Creation of Native and Hybrid hCNGB3 Promoters

In these experiments, new native and hybrid hCNGB3 promoters were created with the goal of enabling hCNGB3 expression in all three types of cone photoreceptors. A pair of oligonucleotide primers was designed for PCR amplification of a 1913 bp DNA fragment immediately 5' of the start codon (ATG) of the hCNGB3 open reading frame (ORF) based on the reference hCNGB3 gene sequence (GenBank acc #NG_016980). The 5' nontranslated region (NTR) of the CNGB3 gene contains the native CNGB3 promoter. The primer sequences used are: pCNGB3-NTR F: 5'-CAGACTAGCCAGAATCACAGATC-3' (SEQ ID NO: 9) and pCNGB3-NTR R: 5'-TCTCCTATAGGCTTCACCT-TGTTG-3' (SEQ ID NO: 10). Using 0.25 µg or 0.5 µg of human genomic DNA (Promega, cat #G1471, lot #305017) as DNA template, PCR amplification was performed using 2×Pfu Ultra HS Mix (Agilent Technologies, cat #600850). The amplification parameters were 5 min at 95° C., followed by 35 cycles of 94° C. for 1 min, 55° C. for 45 sec, and 72° C. for 2 min An amplified DNA fragment of 1913 bp was purified by agarose gel electrophoresis and used as template DNA for PCR amplification to generate shortened NTR sequences 5'-of hCNGB3 gene. Two sets of oligonucleotide primers were designed to amplify 5'-NTR sequences of 1800 bp and 1600 bp, respectively. Sequences of the primer set used to amplify the 1,800 bp 5'-NTR are pCNGB3-NTF F238 Acc65I: 5'-GTTGGGTACCAGCCGCCATCAG-GAATAAAC-3' (SEQ ID NO: 11), and pCNGB-NTR R SacII: 5'-TCTCCGCGGTGGTTCTGAAAACCCTC-3' (SEQ ID NO: 12). Sequences of the primer set used to amplify the 1,600 bp 5'-NTR are pCNGB3-NTR F431 Acc65I: 5'-CATCTTGGTACCACATTCTCTTACAGAGC-3' (SEQ ID NO: 13), and pCNGB3-NTR R XhoI: 5'-ATCT-TCTCGAGGGTGGTTCTGAAAACCCTC-3' (SEQ ID NO: 14). The shortened 5'-NTR sequences were amplified by PCR using 2×Pfu Ultra HS Mix (Agilent Technologies, cat #600850), with PCR amplification parameters of 5 min at 95° C., followed by 35 cycles of 94° C. for 1 min, 54° C. for 45 sec, and 72° C. for 2 min.

DNA was amplified from the 1913 bp 5'-NTR fragment using the primer set of pCNGB3-NTF F238 Acc65I and pCNGB-NTR R SacII. The amplified DNA was digested with Acc65I and SacII endonuclease and inserted into pTR-PR1.7-hGFP that had been digested with Acc65I and SacII to generate plasmid pTR-NTR1800-hGFP.

DNA was amplified from the 1913 bp 5'-NTR fragment using the primer set of pCNGB3-NTR F431 Acc65I and pCNGB3-NTR R XhoI. The amplified DNA was digested with Acc65I/XhoI, and inserted into pTR-CMVenh-PR1.1-hGFP that had been digested with Acc65I/XhoI to generate plasmid pTR-NTR1600-hGFP.

DNA was amplified from the 1913 bp 5'-NTR fragment using the primer set of pCNGB3-NTR F431 Acc65I and pCNGB3-NTR R XhoI. The amplified DNA was digested HpaI/XhoI and inserted into pTR-CMVenh-PR1.1-hGFP that had been digested with SnaBI/XhoI to generate plasmid pTR-CMVenh-NTR1350-hGFP.

The DNA sequence of the expression cassette, including the promoter, hGFP were confirmed by DNA sequencing, and the terminal repeats (TRs) were confirmed by SmaI restriction mapping.

Example 3

In Vivo Efficacy of Cone Specific Promoters from the Native CNGB3 Non-Translated Region in Driving GFP Expression in Retinal Cells The following experiments demonstrated the in vivo efficacy of cone specific promoters from the native CNGB3 non-translated region in driving GFP expression in retinal cells of mice.

Four AAV5 vectors containing a unique promoter driving GFP were constructed and manufactured by the conventional transfection methods. These four vectors include: 1) AAV5-NTR1.8-hGFP which contains an isolated promoter comprising approximately 1.8 kb of the 5'-NTR of the CNGB3 gene as described herein; 2) AAV5-NTR1.6-hGFP which contains an isolated promoter comprising approximately 1.6 kb of the 5'-NTR of the CNGB3 gene as described herein; 3) AAV5-CMVenh-NTR1.4-hGFP which contains an isolated promoter comprising approximately 400 bp of the cytomegalovirus (CMV) enhancer as described herein. and approximately 1.4 kb of the 5'-NTR of the CNGB3 gene as described herein; and 4) AAV5-PR2.1-hGFP which contains the 2.1 KB version of the human red/green opsin promoter (PR2.1) and served as a positive control.

One microliter (1 μl) of vector (2×1012 vg/mL) was injected into the subretinal space of C57bl6 mice of approximately 6-8 weeks of age using standard technique (Timmers et al 2001). A total of 10 eyes were injected with each vector. Mice were sacrificed approximately 6 weeks post injection. The eyes were enucleated and serially sectioned at 10 microns with a cryostat after preparation. Retinal sections were stained with a rabbit polyclonal antibody to hGFP, and lectin PNA conjugated to Alexa Fluor 594. Retinal sections were analyzed by confocal microscopy and images were taken.

Figure 6:
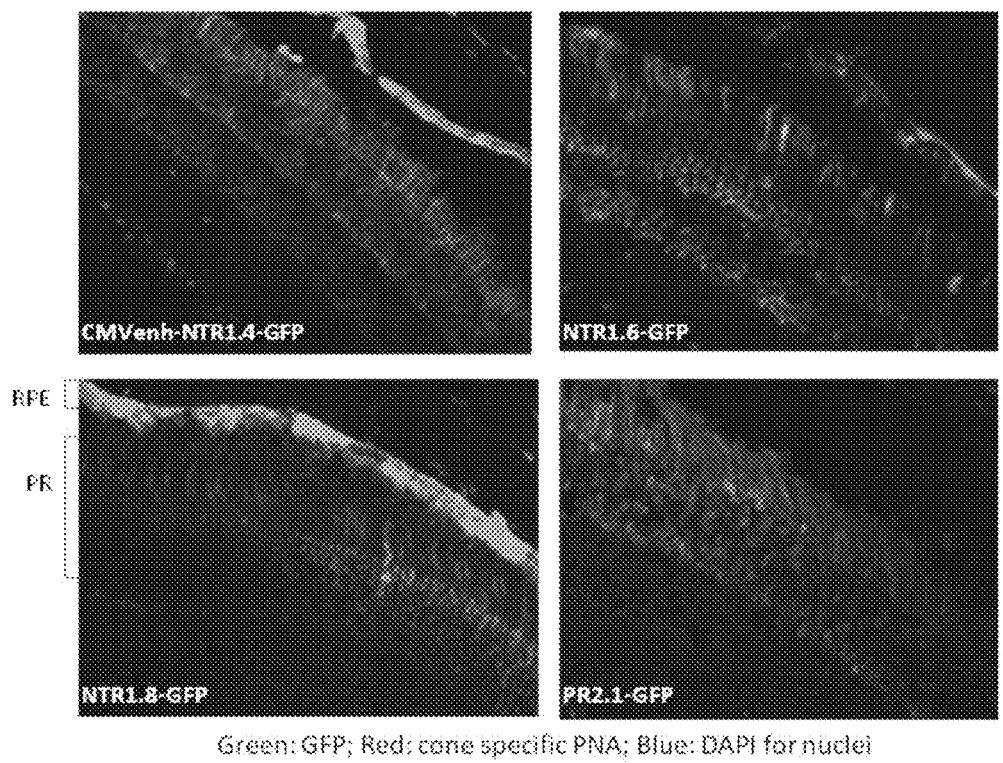
FIG. 6 sets forth images of representative retinal sections. RPE: retinal pigment epithelium; PR: photo receptor. Green: stained for GFP protein expression; Red: stained for cones; Blue: stained for neuclei.

All vectors tested resulted in visible GFP expression in retinal sections. The positive control AAV5-PR2.1-hGFP resulted in relatively strong cone transduction and no transduction in retinal pigment epithelium cells (RPE). On the other hand, AAV5-NTR1.8-hGFP resulted in strong transduction specifically in RPE. AAV5-CMVenh-NTR1.4-hGFP also resulted in strong transduction in RPE and minimal transduction in photo-receptors (PRs) (i.e., rods and cones). For AAV5-NTR1.6-hGFP, only minimal RPE transduction was observed. The results are shown in FIG. 6 and also summarized in Table 1.

TABLE 1

Summary of relative transduction efficiencies for promoter constructs

| Promoter construct | Rod transduction | Cone transduction | RPE transduction |
|---|---|---|---|
| AAV5-CMVenh-NTR1.4-hGFP | + | + | +++ |
| AAV5-NTR1.6-hGFP | +/− | +/− | + |
| AAV5-NTR1.8-hGFP | − | +/− | +++ |
| AAV5-PR2.1-hGFP | ++ | +++ | − |

The NTR1.8 is a strong promoter for RPE cells and is thus useful for RPE related gene therapies.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated promoter comprising the cytomegalovirus (CMV) nucleic acid sequence as set forth in SEQ ID NO: 3 operably linked to a 5' non-transcribed region (5' NTR) of the cyclic nucleotide-gated ion channel beta 3 (CNGB3) nucleic acid sequence as set forth in SEQ ID NO: 4.

2. A transgene expression cassette comprising
   (a) the promoter of claim 1;
   (b) a nucleic acid molecule encoding a protein selected from the group consisting of CNGB3, CNGA3, and GNAT2 under the control of the promoter of step (a); and
   (c) minimal regulatory elements.

3. A nucleic acid vector comprising the expression cassette of claim 2.

4. The vector of claim 3, wherein the vector is an adeno-associated viral (AAV) vector.

5. The vector of claim 4, wherein the AAV vector comprises a nucleic acid molecule encoding AAV protein selected from the group of AAV serotypes consisting of AAV1, AAV2, AAV3, AAV4, AAV5, AAV6, AAV7, AAV8, AAV9, AAV10, AAV11, and AAV12.

6. A kit comprising
   (a) an isolated promoter comprising the cytomegalovirus (CMV) nucleic acid sequence as set forth in SEQ ID NO: 3 operably linked to a 5' non-transcribed region (5'

NTR) of the cyclic nucleotide-gated ion channel beta 3 (CNGB3) nucleic acid sequence as set forth in SEQ ID NO: 4, and (b) instructions for use thereof.

7. A kit comprising (a) the nucleic acid vector of claim 3, and (b) instructions for use thereof.

8. A method of making a recombinant adeno-associated viral (rAAV) vector comprising inserting into an adeno-associated viral vector the promoter of claim 1.

9. The method of claim 8, wherein the rAAV vector comprises a nucleic acid molecule encoding AAV protein selected from the group of AAV serotypes consisting of AAV1, AAV2, AAV3, AAV4, AAV5, AAV6, AAV7, AAV8, AAV9, AAV10, AAV11, and AAV12.

10. A kit comprising (a) the nucleic acid vector of claim 4, and (b) instructions for use thereof.

\* \* \* \* \*